(12) United States Patent
Gazit

(10) Patent No.: US 9,996,922 B2
(45) Date of Patent: Jun. 12, 2018

(54) IMAGE PROCESSING OF ORGANS DEPENDING ON ORGAN INTENSITY CHARACTERISTICS

(71) Applicant: Algotec Systems Ltd., Rochester, NY (US)

(72) Inventor: Tiferet Gazit, Tel-Aviv (IL)

(73) Assignee: Algotec Systems Ltd., Ra'anana (IL)

( * ) Notice: Subject to any disclaimer, the term of this patent is extended or adjusted under 35 U.S.C. 154(b) by 175 days.

(21) Appl. No.: 15/093,803

(22) Filed: Apr. 8, 2016

(65) Prior Publication Data

US 2016/0300351 A1    Oct. 13, 2016

Related U.S. Application Data

(60) Provisional application No. 62/217,987, filed on Sep. 14, 2015, provisional application No. 62/144,552, filed on Apr. 8, 2015.

(51) Int. Cl.
*G06K 9/00* (2006.01)
*G06T 7/00* (2017.01)
(Continued)

(52) U.S. Cl.
CPC ............ *G06T 7/0012* (2013.01); *A61B 6/032* (2013.01); *A61B 6/5211* (2013.01); *G06T 5/002* (2013.01);
(Continued)

(58) Field of Classification Search
CPC ......... A61B 6/032; A61B 6/481; A61B 6/482; A61B 6/5211; G06T 2207/10081; G06T 2207/20004; G06T 2207/20081; G06T 2207/20182; G06T 2207/20208; G06T 2207/30084; G06T 5/002; G06T 5/009;
(Continued)

(56) References Cited

U.S. PATENT DOCUMENTS 6,296,565 B1    10/2001   Kenkel et al.
7,260,249 B2    8/2007    Smith
(Continued)

OTHER PUBLICATIONS

Xiangrong Zhou, Automatic localization of solid organs on 3D CT images by a collaborative majority voting decision based on ensemble learning, Computerized Medical Imaging and Graphics, vol. 36, 2012, pp. 304-313.
(Continued)

*Primary Examiner* — Nirav G Patel

(57) ABSTRACT

A method of processing a medical image comprising an organ, the method comprising: obtaining a medical image; automatically estimating one or more organ intensity characteristics in the image, from contents of a region of the image that appears to correspond, at least in part, to at least a portion of the organ; providing a plurality of sets of organ intensity characteristics, each set a different example of possible intensity characteristics of the organ; choosing one of the plurality of sets, that has organ intensity characteristics that provide a better match than one or more other sets to the estimated organ intensity characteristics of the image; setting values of one or more image processing parameters based on the organ intensity characteristics of the chosen set; and automatically processing the image using said values of image processing parameters.

19 Claims, 14 Drawing Sheets

(51) Int. Cl.
| | |
|---|---|
| *A61B 6/03* | (2006.01) |
| *G06T 5/00* | (2006.01) |
| *A61B 6/00* | (2006.01) |
| *G06T 7/11* | (2017.01) |
| *G06T 7/187* | (2017.01) |
| *G06T 7/155* | (2017.01) |

(52) U.S. Cl.
CPC ............ *G06T 5/009* (2013.01); *G06T 7/0014* (2013.01); *G06T 7/11* (2017.01); *G06T 7/155* (2017.01); *G06T 7/187* (2017.01); *G16H 50/50* (2018.01); *A61B 6/481* (2013.01); *A61B 6/482* (2013.01); *G06T 2207/10081* (2013.01); *G06T 2207/20004* (2013.01); *G06T 2207/20076* (2013.01); *G06T 2207/20081* (2013.01); *G06T 2207/20182* (2013.01); *G06T 2207/20208* (2013.01); *G06T 2207/30056* (2013.01); *G06T 2207/30084* (2013.01); *G06T 2207/30101* (2013.01)

(58) Field of Classification Search
CPC ....... G06T 7/0012; G06T 7/0014; G06T 7/11; G06T 7/187
See application file for complete search history.

(56) References Cited

U.S. PATENT DOCUMENTS

| | | | |
|---|---|---|---|
| 8,170,306 | B2 | 5/2012 | Yu et al. |
| 2008/0279431 | A1* | 11/2008 | Kitamura ........... A61B 1/00009 382/128 |
| 2012/0236995 | A1 | 9/2012 | Eusemann et al. |
| 2013/0274589 | A1 | 10/2013 | Gross et al. |
| 2014/0005538 | A1 | 1/2014 | Florent et al. |
| 2014/0254909 | A1* | 9/2014 | Carmi ................... A61B 6/032 382/131 |
| 2016/0038248 | A1* | 2/2016 | Bharadwaj .......... G06F 3/04847 715/771 |
| 2016/0300359 | A1* | 10/2016 | Lachner ................ G06T 7/0012 |

OTHER PUBLICATIONS

J. A. Sethian, Level Set Methods and Fast Marching Methods: Evolving interfaces in computational geometry, fluid mechanics, computer vision, and materials science, Computer Vision, and Materials Science, Cambridge University Press, 1996, Text Book, ISBN-13 098-0-521-64204-0 hardback, pp. 1-2.
Hyunjin Park et al., Construction of an Abdominal Probabilistic Atlas and its Application in Segmentation, IEEE Transactions on Medical Imaging, vol. 22, No. 4, Apr. 2003, pp. 483-492.
Chien-Cheng Lee et al., Identifying Multiple Abdominal Organs From CT Image Series Using a Multimodule Contextual Neural Network and Spatial Fuzzy Rules, IEEE Transactions on Information Technology in Biomedicine, vol. 7, No. 3, Sep. 2003, pp. 208-217.
A. Criminisi et al., Regression forests for efficient anatomy detection and localization in computed tomography scans, Medical Image Analysis, vol. 17, 2013, pp. 1293-1303.
A. Bhattacharyya, On a measure of divergence between two statistical populations defined by their probability distributions, Wikipedia, 2015, pp. 1-4.
Calvin C. Gotlieb et al., Texture Descriptors Based on Co-occurrences Matrices, Computer Vision, Graphics, and Image Processing, vol. 51, 1990, pp. 70-86.
Yi Wang et al., Studies on Tissue Characterization by Texture Analysis with Co-occurrence Matrix Method Using Ultrasonography and CT Imaging, J. Med. Ultrasonics, vol. 29, Winter 2002, pp. 211-223 (Translation of Original Contribution).
Commonly assigned: U.S. Appl. No. 14/666,386, Organ-Specific Image Display, by Gazit et al., filed Mar. 24, 20015.
Commonly assigned: U.S. Appl. No. 61/974,077, Organ-Specific Image Display, by Gazit et al., filed Apr. 2, 2014.

* cited by examiner

IMAGE PROCESSING OF ORGANS DEPENDING ON ORGAN INTENSITY CHARACTERISTICS

CROSS REFERENCE TO RELATED APPLICATIONS

This application claims the benefit of U.S. Provisional application U.S. 62/217,987 provisionally filed on Sep. 14, 2015, entitled IMAGE PROCESSING OF ORGANS DEPENDING ON ORGAN INTENSITY CHARACTERISTICS in the name of Tiferet T. Gazit, incorporated herein by reference in entirety.

This application claims the benefit of U.S. Provisional application U.S. 62/144,552 provisionally filed on Apr. 8, 2015, entitled ORGAN DETECTION AND SEGMENTATION in the name of Tiferet T. Gazit, incorporated herein by reference in entirety.

TECHNICAL FIELD

The invention relates generally to the field of image processing, and in particular to medical image processing or organs. The present disclosure, in some embodiments thereof, relates to image processing of an organ or other structure in a medical image and, more particularly, but not exclusively, to automatically detecting and segmenting a target organ.

BACKGROUND OF THE INVENTION

U.S. Pat. No. 7,260,249 (Smith) describes a "technique [that] applies pre-programmed rules that specify the manner in which medical image data is to be processed with different rules being based on different doctors' preferences, such as during contrast agent studies. One embodiment of the invention has application in contrast studies, where a contrast agent is applied to the tissues of the patient in order to provide enhanced images that depict tissue behavior during 'uptake' and 'washout' of the contrast agent. A first set of images is created before the contrast agent is injected. The time at which the contrast agent is injected is carefully tracked, and additional sets of images are created at selected time intervals."

U.S. 2012/0236995 (Eusemann et al.) describes a "system [that] automatically adaptively determines contrast agent administration parameters for use in a CT scan imaging system. The system includes predetermined information associating a contrast agent type, contrast agent administration parameters, an imaging system X-ray tube voltage, a type of imaging procedure, and an anatomical region to be imaged. The [system] receives data identifying a type of imaging procedure or an anatomical region to be imaged, [and] uses the information in automatically identifying contrast agent parameters and X-ray tube voltage for use [with] a patient."

U.S. 2013/0274589 (Gross et al) describes injecting ultrasound contrast agent together with CT or MRI contrast agent into the bloodstream. The location of the ultrasound contrast agent is continuously monitored with ultrasound imaging, and CT images are made only when the contrast agent is at the desired location, thereby avoiding the need to make many CT images at frequent time intervals, which would result in a high x-ray dose to the patient. In the case of MRI, the location of the contrast agent, as determined by the ultrasound imaging, can be used to interpret the MRI image, since the location of the contrast agent may change significantly during the long acquisition time of the MRI.

U.S. 2014/0005538 (Florent et al.) describes "normalizing perfusion [image] data based on the amount of contrast agent" present in a blood vessel, which is "deduced from the estimation of the total volume flow at this location."

U.S. Pat. No. 8,170,306 (Yu et al.) describes "A recognition pipeline [that] automatically partitions a 3D image of the human body into regions of interest (head, rib cage, pelvis, and legs) and correctly labels each region. The recognition is robust to image variations, and does not require the user to provide any knowledge about the contained regions of interest within the image."

U.S. Pat. No. 6,296,565 (Inbar et al.) describes "a viewbox with a display surface adapted to hold a film. A camera views the display surface and is connected to a controller. The invention is especially suitable for viewing medical images such as X-ray films or transparencies which are produced by hardcopy devices associated with digital medical imaging equipment." The device can be used for viewing "a chest film, wherein determination of lung position enables the masking out of the abdomen and backbone which is much more transparent than the nearby lungs, so that it dazzles an operator viewing the lungs." The patent describes automated "methods [that] are used to determine the extent of the lungs."

SUMMARY OF THE INVENTION

An aspect of some embodiments of the invention concerns a method of image processing of a medical image which could potentially have different organ intensity characteristics, matching it with one of several sets of different organ intensity characteristics, and taking into account the matched organ intensity characteristics when processing the image.

There is thus provided, in accordance with an exemplary embodiment of the invention, a method of processing a medical image comprising an organ, the method comprising: a) obtaining a medical image; b) automatically estimating one or more organ intensity characteristics in the image, from contents of a region of the image that appears to correspond, at least in part, to at least a portion of the organ; c) providing a plurality of sets of organ intensity characteristics, each set a different example of possible intensity characteristics of the organ; d) choosing one of the plurality of sets, that has organ intensity characteristics that provide a better match than one or more other sets to the estimated organ intensity characteristics of the image; e) setting values of one or more image processing parameters based on the organ intensity characteristics of the chosen set; and f) automatically processing the image using said values of image processing parameters.

Optionally, choosing one of the plurality of sets or organ intensity characteristics is done automatically, using as input data the estimated one or more organ intensity characteristics, and data defining the plurality of sets of organ intensity characteristics.

Optionally, setting values of the one or more image processing parameters is done automatically, using as input data the organ intensity characteristics of the chosen set.

Optionally, one or more of the sets are generated using a theoretical model for expected organ intensity characteristics of the organ under different conditions of acquiring an image of the organ.

Alternatively or additionally, two or more of the sets are generated from a plurality of training images acquired from subjects under different conditions and grouped in clusters, each of the two or more sets generated from a different cluster of the training images.

In an embodiment of the invention, the method comprises: a) obtaining information about organ intensity characteristics for each of the training images; b) grouping the training images into clusters according to the information about organ intensity characteristics; and c) for each of a plurality of the clusters, finding representative information about the organ intensity characteristics for the training images in that cluster; wherein providing the sets of organ intensity characteristics comprises providing the representative information for the training images in the cluster that each set is generated from, for the sets that are generated from the training images.

Optionally, estimating the organ intensity characteristics comprises determining information on image texture from the contents of the image in the region.

Alternatively or additionally, estimating the organ intensity characteristics comprises determining information on an intensity distribution of voxels from the contents of the image in the region, the sets of organ intensity characteristics comprise information on intensity distributions of voxels, and choosing one of the sets comprises choosing a set for which the information on an intensity distribution provides a better match than the information on an intensity distribution of another set to the information intensity distribution of voxels in the region of the image.

Optionally, choosing a set for which the information on an intensity distribution of voxels provides a better match to the information on an intensity distribution of voxels in the region comprises choosing a set for which the information on an intensity distribution of voxels provides a better match of a plurality of independent parameters.

Optionally, at least two of the sets of organ intensity characteristics differ from each other in exemplifying different results of contrast agent use or lack of use in the organ, and choosing one of the sets comprises choosing a set which exemplifies results of contrast agent use or lack of use that provide a better match than one or more other sets to the results of contrast agent use or lack of use in the image.

Optionally, the image processing parameters comprise one or more of information on a distribution of voxel intensities, and information on a distribution of voxel intensity gradients, specific to the chosen set of organ intensity characteristics.

Optionally, the image processing parameters comprise information on a distribution of magnitudes of intensity gradient expected in an interior of the organ, and information on a distribution of magnitudes of intensity gradient expected along a boundary of the organ, specific to the chosen set of organ intensity characteristics.

Optionally, setting values of one or more image processing parameters comprises choosing between two or more qualitatively different image processing algorithms.

In an embodiment of the invention, processing the image comprises evaluating a local characteristic of one or more voxels in the image.

Optionally, evaluating the local characteristic of one or more voxels provides information on whether the voxels are likely to belong to the organ, the method also comprising segmenting the organ in the image using said information.

Optionally, the method also comprises: a) making a new estimate of the organ intensity characteristics based on the segmentation of the organ; b) setting new values of one or more image processing parameters based on the new estimate of the organ intensity characteristics; and c) segmenting the organ in the image again using said new values of image processing parameters.

Optionally, the method also comprises: a) finding at least an approximate bounding region of the organ in the image, wherein the region of the image used for estimating organ intensity characteristics is the bounding region; b) finding a new bounding region of the organ based on the segmentation of the organ; c) finding the organ intensity characteristics based on the new bounding region; d) setting new values of one or more image processing parameters based on the organ intensity characteristics found in (c), and on the new bounding region; and e) segmenting the organ in the image again, using said new values of image processing parameters.

Optionally, the different sets of organ intensity characteristics differ from each other in exemplifying different results of contrast agent use or lack of use in the organ, choosing one of the sets comprises choosing a set exemplifying results of contrast agent use or lack of use that provide a better match than one or more other sets to the results of contrast agent use or lack of use in the image, and evaluating the local characteristic comprises evaluating whether the one or more voxels are likely to belong to the organ based on whether their intensity, intensity gradient, or both, are within a range expected for voxels of the organ according to the training images of the chosen cluster, and segmenting the organ comprises finding a core region of voxels that are likely to belong to the organ according to said evaluation.

Optionally, segmenting the organ also comprises using a region-growing algorithm, starting from one or more seed voxels in the core region.

Optionally, the different sets of organ intensity characteristics differ from each other in exemplifying different results of contrast agent use or lack of use in the organ, choosing one of the sets comprises choosing a set exemplifying results of contrast agent use or lack of use that provide a better match than one or more other sets to the results of contrast agent use or lack of use in the image, and evaluating the local characteristic of a voxel comprises evaluating a cost function that depends on a degree of similarity of one or more of the intensity and the intensity gradient of the voxel to values expected for voxels of the organ according to the training images of the chosen cluster, and segmenting the organ comprises using a region-growing algorithm with said cost function.

Optionally, the method also includes finding at least an approximate bounding region of the organ in the image, wherein the region of the image used for estimating organ intensity characteristics is the bounding region.

In an embodiment of the invention, processing the image comprises changing the intensity values of one or more voxels of the image.

Optionally, the image processing parameters comprise an expected minimum magnitude of intensity gradient at the edge of the organ, and processing the image comprises anisotropically smoothing the image with less smoothing along an intensity gradient that is greater than the expected minimum magnitude than perpendicular to the intensity gradient.

Optionally, the image processing parameters comprise a range of intensity for which the organ has structure that would be more easily visible if the contrast were increased in that range, and processing the image comprises increasing the contrast in that range.

There is further provided, in accordance with an exemplary embodiment of the invention, a system for processing a medical image comprising an organ, the system comprising: a) an input device the receives a digital test image; b)

a data storage device that stores data defining a plurality of sets of organ intensity characteristics, each set a different example of possible intensity characteristics of the organ; and c) a data processor with access to the test image and the data defining the sets of organ intensity characteristics, programmed to: i) estimate one or more organ intensity characteristics in the image, from contents of a region of the image that appears to correspond, at least in part, to at least a portion of the organ; ii) obtain a choice of one of the plurality of sets, that has organ intensity characteristics that provide a better match than one or more other sets to the estimated organ intensity characteristics of the image; iii) set values of one or more image processing parameters based on the organ intensity characteristics of the chosen set; and iv) process the image using said values of image processing parameters.

Optionally, the data processor is programmed to obtain the choice of one of the plurality of sets by choosing one of the plurality of sets automatically, based on the estimated organ intensity characteristics of the image.

Alternatively or additionally, they system also comprises a user interface, and the data processor is programmed to use input from a user through the user interface, to obtain the choice of one of the plurality of sets.

There is further provided, in accordance with an exemplary embodiment of the invention, a method of finding medical images with a field of view expected to include a target organ in the abdomen, the method comprising: a) obtaining a plurality of medical images acquired from one or more subjects, at least some of the images having different fields of view, each of the images having known orientation with respect to the subject's body; b) automatically determining, in each of the images, whether or not the lungs are present, and automatically segmenting the lungs, at least roughly, if they are present; c) automatically determining, from the contents of the images, including the presence or absence of the lungs and the location of the lungs if they are present, which images have a field of view that is expected to include the target organ, and which images do not.

Optionally, at least some of the images obtained have one or more of different resolution, different image characteristics affected by contrast agent use of lack of use, and different noise level.

Optionally, the method also comprises: a) automatically determining, from the contents of the images, which images have a field of view that includes both an abdomen region and a chest region, or which images have a field of view that includes both an abdomen region and a pelvis region, or which images have a field of view that includes both an abdomen region and one or both or a chest region and pelvis region, or which images have a field of view that includes a chest region, an abdomen region, and a pelvis region; and b) automatically dividing each of those images into a plurality of separate sub-images, each sub-image showing a different one of the regions, chest, abdomen or pelvis, determined to be in the field of view of the image.

Optionally, determining which images have a field of view that is expected to include the organ comprises: a) for those images that are determined to include at least part of the lungs, determining whether a bottom edge of the field of view of the image is at least a threshold distance below the lowest lung voxel; and b) if the bottom edge of the field of view is at least the threshold distance below the lowest lung voxel, determining that the field of view of the image is expected to include the target organ.

Optionally, determining which images have a field of view that is expected to include the organ comprises: a) for those images that are determined to include at least part of the lungs, determining whether a bottom edge of the field of view of the image is at least a threshold distance below the lowest lung voxel; and b) if the bottom edge of the field of view is less than the threshold distance below the lowest lung voxel, determining that the field of view is not expected to include the target organ.

Optionally, the threshold distance is between 30 and 40 cm.

Optionally, determining which images have a field of view that is expected to include the organ comprises: a) for those images that are determined not to include any of the lungs, determining whether a top edge of the field of view of the image is empty of any part of the subject's body; and b) if the top edge of the field of view is empty of any part of the subject's body, determining that the field of view is not expected to include the target organ.

Optionally, determining which images have a field of view that is expected to include the organ comprises: a) for those images that are determined not to include any of the lungs, attempting to obtain a segmentation of the large leg bones; b) for those images that are determined not to include any of the lungs, and that include the large leg bones according to the attempted segmentation of the large leg bones, determining whether a top edge of the image is at least a threshold distance above a highest voxel of the large leg bones; and c) for those images for which the top edge of the image is at least the threshold distance above the highest voxel of the large leg bones, determining that the field of view of the image is expected to include the target organ.

Optionally, determining which images have a field of view that is expected to include the organ comprises: a) for those images that are determined not to include any of the lungs, attempting to obtain a segmentation of the large leg bones; b) for those images that are determined not to include any of the lungs, and that do include the large leg bones according to the attempted segmentation of the large leg bones, determining whether a top edge of the image is at least a threshold distance above a highest voxel of the large leg bones; and c) for those images for which the top edge of the image is not at least the threshold distance above the highest voxel of the large leg bones, determining that the field of view of the image is not expected to include the target organ.

Optionally, the threshold distance is between 28 and 38 cm.

Optionally, determining which images have a field of view that is expected to include the organ comprises: a) for those images that are determined not to include any of the lungs, attempting to obtain a segmentation of the large leg bones; b) for those images that are determined not to include any of the lungs, and not to include any of the large leg bones, determining whether an axial slice of the image that contains a largest area of voxels that lie within the subject's body has an area of voxels within the subject's body greater than a threshold area; and c) for those images for which the largest area of voxels that lie within the subject's body is not greater than the threshold area, determining that the field of view of the image is not expected to include the target organ.

Optionally, determining which images have a field of view that is expected to include the organ comprises: a) for those images that are determined not to include any of the lungs, attempting to obtain a segmentation of the large leg bones; b) for those images that are determined not to include any of the lungs, and not to include any of the large leg bones, determining whether an axial slice of the image that contains a largest area of voxels that lie within the subject's body has an area of voxels within the subject's body greater than a threshold area; and c) for those images for which the largest area of voxels that lie within the subject's body is greater than the threshold area, determining that the field of view of the image is expected to include the target organ.

Optionally, the threshold area is between 250 and 400 square centimeters.

There is further provided, in accordance with an exemplary embodiment of the invention, a system for finding medical images with a field of view expected to include a target organ in the abdomen, the system comprising: a) an input device that receives digital medical images of one or more subjects, including information on an orientation of each image with respect to the subject's body; and b) a data processor with access to the medical images, programmed to: i) determine, in each of the images, whether or not the lungs are present, and to segment the lungs, at least roughly, if they are present; ii) determine, from the contents of the images, including the presence or absence of the lungs and the location of the lungs if they are present, which images have a field of view that is expected to include the target organ, and which images do not.

There is further provided, in accordance with an exemplary embodiment of the invention, a method of automatically selecting for registration medical images covering a selected region of a subject's body, the method comprising: a) providing a plurality of medical images of the subject, some of which cover the selected region of the subject's body, and at least one of which covers a different region of the subject's body and does not cover the selected region; b) automatically determining, from the contents of the images, which of the images cover the selected region; and c) selecting for registration the images covering the selected region.

Optionally, the method also comprises automatically registering the images selected for registration.

Optionally, the selected region is the abdomen, the provided medical images have known orientation with respect to the subject's body, and automatically determining which images cover the selected region comprises: a) automatically determining, in each of the images, whether or not the lungs are present, and automatically segmenting the lungs, at least roughly, if they are present; b) automatically determining, from the contents of the images, including the presence or absence of the lungs and the location of the lungs if they are present, which images have a field of view that is expected to include the abdomen, and which images do not.

There is further provided, according to an exemplary embodiment of the invention, a system for automatically selecting for registration medical images covering a selected region of a subject's body, the system comprising: a) an input device that receives digital medical images; and b) a data processor with access to the medical images, programmed to: i) determine, from the contents of the images, which of the images cover the selected region; and ii) select for registration the images covering the selected region.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit", "module" or "system". Furthermore, aspects of the present invention may take the form of a computer program product embodied in one or more computer readable medium(s) having computer readable program code embodied thereon. Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as image processing, sensor analysis and/or database retrieval, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced. In the drawings.

DESCRIPTION OF EMBODIMENTS OF THE INVENTION

Figure 1:
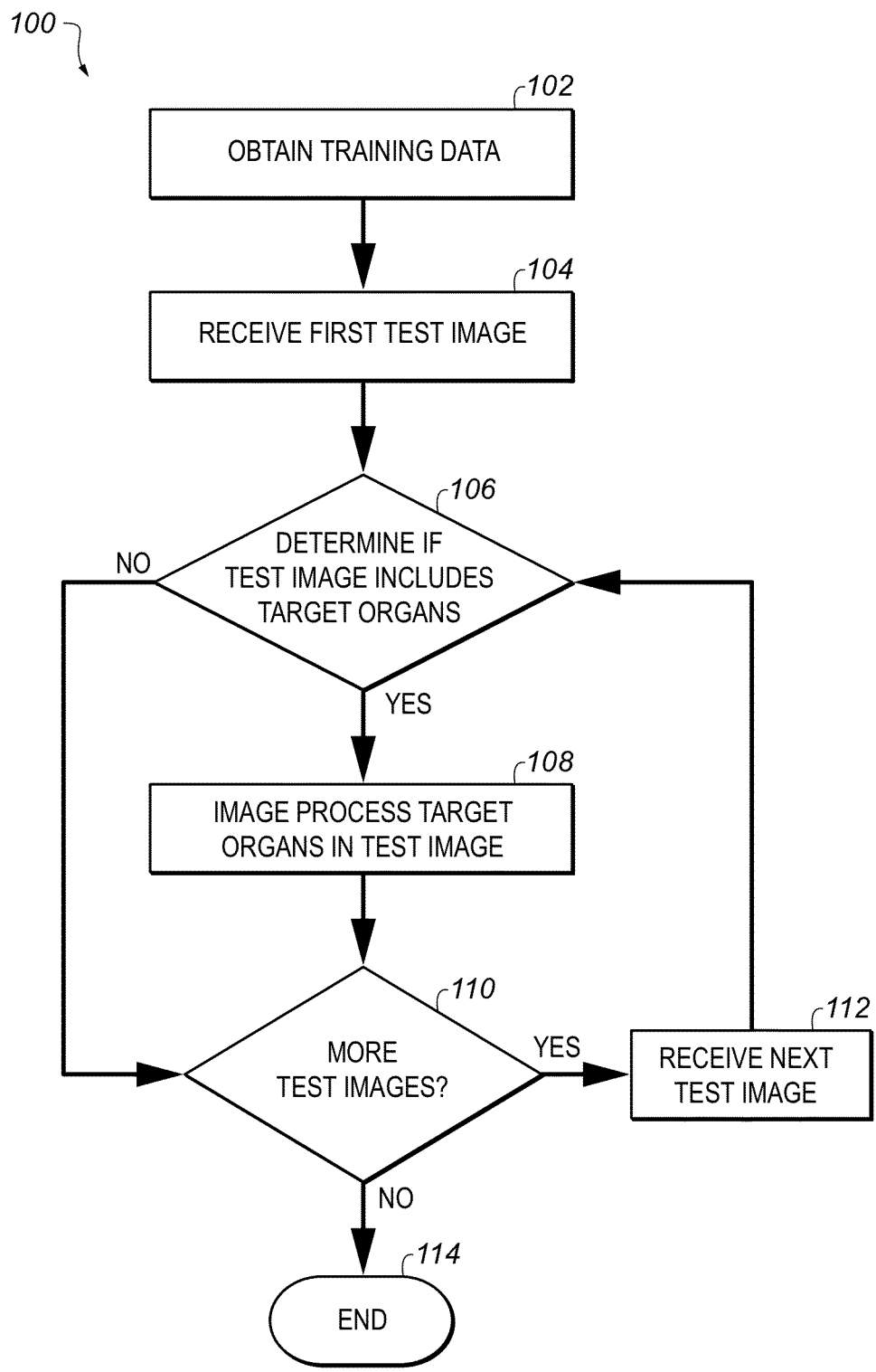
FIG. 1 is a flow chart showing a method of obtaining training data from training medical images, and using the training data to image process one or more target organs in a test medical image, according to an exemplary embodiment of the invention.

The present invention, in some embodiments thereof, relates to image processing of an organ or other structure in a medical image and, more particularly, but not exclusively, to automatically detecting and segmenting a target organ.

An aspect of some embodiments of the invention concerns a method of image processing of medical images, which have different organ intensity characteristics for at least one target organ. The organ intensity characteristics of the image are compared to several pre-defined sets of organ intensity characteristics, each set exemplifying different organ intensity characteristics that might be found in images made of the target organ under different conditions, and one of the sets is chosen as making the best match, or at least a better match than other sets, to the organ intensity characteristics of the image. The chosen set of organ intensity characteristics, and optionally also the actual organ intensity characteristics of the image, are used to set values of image processing parameters, which are then used to process the image, for example to segment the image, or to perform anisotropic smoothing of the image.

As used herein, "medical image" means imaging data, acquired from a subject using a medical imaging device, and located in a computer memory or data storage medium, such as a hard drive, optical disk, or flash memory, not just data in an abstract sense, even when that is not stated explicitly. It should be understood that at least some of the actions described as being performed on or with a medical image, such as determining organ intensity characteristics of the image, or segmenting, smoothing, or otherwise processing the image, or determining whether the image has a field of view that includes abdominal organs, are done automatically, by a computing device, such as a general purpose computer or specialized digital circuitry, executing instructions in specialized software that is designed for the actions being performed. However, in some embodiments of the invention, some actions, such as choosing which set of organ intensity characteristics provides a best match or a better match to the organ intensity characteristics of the image being processed, may be done manually, and the results entered into a computing device as data through a user interface. The input for the software, such as a medical image, the intermediate results, such as a set of organ intensity characteristics determined for an input image, or image processing parameters to be used for processing an input image, or a segmentation mask of the lungs, and the final output, such as a smoothed image, or a segmented image, or a segmentation mask of a target organ, or a yes/no answer to the question of whether the field of view includes a specified region such as the abdomen, all consist of data located in a computer memory or data storage medium.

In general, medical images have a large quantity of data, typically many megabytes, and the image processing and analysis performed by a computer running software are done using methods that are only suitable for use by a computer, even if there are alternative manual methods of accomplishing the same goals, such as having a human expert segment an image. The methods used by a human expert to segment a medical image are generally very different from the methods used by a computer performing automatic segmentation of a medical image, and similarly for other kinds of image processing. It should also be understood that the methods described herein represent an advance in the technical field of medical image processing, which can be useful, for example, in diagnosing or monitoring patients with medical conditions. These methods do not constitute the mere use of a computer to perform routine actions by essentially the same methods that are used by people performing the actions manually. In some cases, accurate manual delineation of organ boundaries in 3D data, and certainly manual image processing such as smoothing or organ-specific image windowing, are far too time consuming to be included in any reasonable clinical routine, and so these processes become useful only if advanced methods are developed that allow them to be done automatically with a computer, or semi-automatically with only a relatively small amount of user input.

In some embodiments of the invention, at least some of the sets of organ intensity characteristics are found from training images of the target organ acquired under a range of different conditions, with the training images grouped into clusters that each contains one or more images with similar organ intensity characteristics. Each of those sets of organ intensity characteristics is then learned from one of the clusters of training images. In some embodiments of the invention, instead of or in addition to defining sets of organ intensity characteristics based on clusters of training images made from real subjects, a theoretical model is used to predict organ intensity characteristics expected for images of an organ acquired under different conditions. The model is optionally used to generate a plurality of sets of organ intensity characteristics, one set for each of a plurality of different conditions for acquiring an image of the organ. Optionally, one or more sets are generated by the model, and additionally one or more other sets are based on training images made from real subjects, under different conditions than the conditions assumed in the model.

The different conditions include, for example, acquiring images with different types or amounts of contrast agent, different timing or different locations where contrast agent is introduced, or from patients with different rates of blood perfusion in the organ, or with different disease states, as will be explained in more detail below.

Tests of the method done by the inventor have involved using training images acquired from subjects, and clustering the training images, in order to generate the sets of organ intensity characteristics, and the description herein sometimes refers to matching the image to a cluster of training images. Similarly, the description also sometimes refers to matching the image to training data obtained from a cluster of training images, or matching the image to a set of organ intensity characteristics that corresponds to a cluster of training images. But it should be understood that the method can be used with any source of different sets of organ intensity characteristics for matching the image to, including modeled sets of organ intensity characteristics.

As used herein, organ intensity characteristics mean intensity characteristics of a region of the image that appears to correspond, at least in part, to at least a portion of the organ. For example, the intensity characteristics may comprise an intensity distribution of the region, or a distribution of intensity gradients, or a distribution of quantities involving higher derivatives of intensity, such as vesselness or hollowness, or a distribution of textures, or information on any of these distributions, for example a mean, median, standard deviation, or other moment of any of these distributions, or a histogram approximating any of these distributions. The distributions need not be distributions of these quantities over the entire region, but could be distributions over only a part of the region, or could be non-uniformly weighted over the region, for example giving higher weight to voxels that are considered more likely to belong to the organ, for example based on a probabilistic atlas of the location of the organ.

The different sets of organ intensity characteristics correspond, for example, to different results of contrast agent use, or lack of use. Additionally or alternatively, different organ intensity characteristics are due to disease states, such as pneumonia in the lungs or cirrhosis in the liver, to age, which can affect bone density for example, or due to other individual differences. The different results of contrast agent use are due, for example, to whether or not contrast agent is used at all, and, among images where contrast agent is used, to using different types of contrast agent, different quantities of contrast agent, different ways of administering contrast agent, such as oral or intravenous, different timing between introducing the contrast agent and acquiring the image, and differences in the subjects, for example differences in their blood circulation, differences in the size and blood supply of the organ, and differences in tissue characteristics which can affect blood diffusion within the organ, all of which can affect the amount of contrast agent reaching the organ, and its distribution within the organ. As used herein, "different results of contrast agent use" and similar phrases implicitly include all of these factors. The matching set of organ intensity characteristics of each image is chosen, and different values of image processing parameters are used in the image processing, depending on the matching set of organ intensity characteristics chosen for that image. It should be understood that two images having different organ intensity characteristics due to different results of contrast agent use need not mean that the images have different amounts of contrast overall, but could mean, for example, that the images have a different spatial distribution of contrast within the organ, or, for example, that one image has higher contrast in darker parts of the image, while the other image has higher contrast in brighter parts of the image.

Optionally, if at least some of the sets of organ intensity characteristics are each based on a different cluster of training images, the training images are grouped into the clusters based on the organ intensity characteristics of the image, for example based on how much contrast the image has, and images with similar organ intensity characteristics are grouped together in the same cluster. Alternatively, the images are grouped into clusters based partly or entirely on other information, for example based on metadata supplied when the image was acquired, which provide information on the contrast agent protocol used in acquiring the image, and images are clustered together, for example, when they were acquired using similar contrast agent protocols. Regardless of the grouping criteria, the group into clusters of the training images may be done automatically, manually, or semi-automatically.

Optionally, the clusters of training images are not overlapping. Alternatively, some of the training images are included in more than one cluster, but on average the training images in each cluster have different organ intensity characteristics. Using overlapping clusters of training images is potentially advantageous if there are a limited number of training images available, and overlapping clusters allows more images to be included in each cluster, possibly resulting in better statistics than if the clusters were not overlapping and had fewer images in them. But using non-overlapping clusters of training images has the potential advantage that it may more accurately distinguish between the different sets of organ intensity characteristics.

Optionally, the chosen set is the one which best matches the organ intensity characteristics of the image. Alternatively, the chosen set is one that is clearly a better match than one or more other sets, even if it is uncertain which set is the best match. Optionally, the sets of organ intensity characteristics consist of a finite number of sets, each representing a range of values of the organ intensity characteristics, for example based on a cluster of training images that has similar but not identical organ intensity characteristics. An example of such sets is shown below, in FIG. 2, where training images of a left kidney were grouped into four clusters, each cluster containing images with similar results of contrast agent use or lack of use, and each cluster is used to generate one of the four sets of organ intensity characteristics. Alternatively, there is a continuum of different sets of organ intensity characteristics, each set representing, for example, a different linear combination of a finite number of basis sets of organ intensity characteristics. In that case, matching the organ intensity characteristics of the image to one of the sets would mean finding coefficients of the basis sets that would lead to a linear combination of the basis sets of organ intensity characteristics that makes the best match, or at least a better match than another linear combination, to the organ intensity characteristics of the image.

In some embodiments of the invention, each of the sets of organ intensity characteristics is explicitly stored as data in a computer memory or digital storage medium, for example data comprising a mean and standard deviation of intensity, or a histogram of intensity, for each set of organ intensity characteristics. This is typically true, for example, when there are a relatively small number of sets of organ intensity characteristics, such as the four sets described above for the left kidney. In other embodiments of the invention, for example when there are a very large or effectively infinite number of sets of organ intensity characteristics, each set need not be stored explicitly as data representing that set, but data is still stored, in a computer memory or digital storage medium, that defines the sets of organ intensity characteristics, and allows each set of organ intensity characteristics to be generated when needed. For example, if the sets of organ intensity characteristics consist of any linear combination of a plurality of basis sets, then optionally data is stored for each of the basis sets, and data for any desired linear combination can be generated by a computer executing the method, when needed, from the data stored for the basis sets, and from the coefficients of the desired linear combination.

Optionally, the image processing comprises evaluating a local characteristic of one or more voxels in the image, and the evaluation of the local characteristic is used to segment a target organ in the image, determining which voxels are likely to belong to the target organ. For example, it is determined which voxels in the image, or in a region of the image, have values of intensity, intensity gradient, and/or a more complicated local property such as vesselness or hollowness, that make it likely that the voxel belongs to the target organ, and which voxels have values that make it likely that they do not belong to the target organ. The ranges of values of these quantities that make it likely that the voxel belongs or does not belong to the target organ depend in general on the organ intensity characteristics, since, for example, higher contrast images will have a different range of intensities, intensity gradients, etc., in the target organ, than lower contrast images. Optionally, as described below in 818 of FIG. 8, the set of voxels that have values that make them likely to belong to the target organ comprise a rough segmentation mask of the target organ, or at least of a core region that is especially likely to belong to the target organ, even if the rough segmentation mask does not include all of the target organ. Alternatively, only some of the voxels in the rough segmentation mask are considered to be in the core region, and other criteria are also required in order for a voxel to be part of the core region, for example the voxel must also have a high probability of belonging to the target organ according to a probabilistic atlas, as described below in 822 of FIG. 8. Optionally, the terms "rough segmentation" and "core region" also refer to these sets of voxels augmented by other voxels, for example by morphological filling operations as described below in 820 of FIG. 8, even though the additional voxels do not have values of the local characteristics that make them likely to belong to the target organ. Optionally, a region-growing algorithm is used to segment the target organ, optionally starting with one or more seed voxels in the rough segmentation mask or in the core region, using a cost function that is a local characteristic of the voxels, and the cost function is evaluated in the course of running the region-growing algorithm.

Alternatively, the image processing comprises modifying or enhancing the image in some way. For example, the image is anisotropically smoothed, reducing noise in the interior and exterior of a target organ, but not blurring the sharpness of the boundaries of the organ. The parameters for doing this will in general depend on the organ intensity characteristics, especially when they are due to different results of contrast agent use or lack of use, because the intensity gradient expected for the boundary of a target organ will generally be higher for images of higher contrast. In another example, the contrast of the image is changed, in order to make a particular type of feature or structure of a target organ, for example a lesion, more easily visible when the image is viewed. For example, this may be done by automatically selecting an optimal set of intensity windowing parameters for viewing the image, as described for example in U.S. Ser. No. 14/666,386 titled "Organ-Specific Image Display," filed Mar. 24, 2015, incorporated herein in its entirety. In general, the parameters for changing the contrast of the image in this way will depend on the organ intensity characteristics, for example on the contrast of the image before image processing.

Optionally, the organ intensity characteristics are learned from the contents of the image, for example from information on a distribution of intensities in a region of the image, for example a bounding region of the target organ in the image, even without making use of any data on contrast agent use that is supplied with the image. Such scanning metadata is often unreliable, can differ from hospital to hospital and from technician to technician, and can even be missing altogether. In addition, such scanning metadata generally provides information only on the contrast agent administration protocol, and not on the individual patient's physiological factors that can influence the timing, quantity, and dispersion of the contrast agent within each organ.

Optionally, information on a distribution of intensities, in the target organ and/or its vicinity, is obtained first from each of a set of training images of that organ, including a variety of different organ intensity characteristics, for example due to different results of contrast agent use, and the training images are clustered according to their organ intensity characteristics. Optionally, an average, possibly a weighted average, is found for the information on the distribution of intensities for all the training images in each cluster, so that one set of information on the distribution of intensities is found to represent each cluster, and only those averages for each cluster are used as the corresponding set of organ intensity characteristics. Optionally, the training images have been previously segmented, for example manually or in any other way, so that the distribution of intensities in the target organ, and the distribution of intensities outside the target organ but in its vicinity, can be learned from them.

Alternatively, instead of or in addition to using distributions of intensity, distributions of quantities that depend on spatial variations in intensity are used, for example distributions of intensity gradient, or of higher derivatives of intensity or quantities that are derived from them, such as vesselness or hollowness, or distributions of more complicated quantities, such as texture. It should be understood that, in the following description, whenever distributions of intensities are mentioned, distributions of quantities that depend on spatial variations in intensity are optionally used instead or in addition.

The characteristics of the image being processed are then learned by comparing information on the distribution of intensities in a region of the image, for example in or near the target organ, to the corresponding information for the different clusters of training images. A cluster is then selected for which the information on the distribution of intensities provides a good match to that of the image being processed.

Optionally, the information on intensity distribution includes one or more of an average of intensity such as a mean, median or mode of intensity, a standard deviation of intensity, other measures of width of the intensity distribution such as full width at half maximum, higher moments of the intensity distribution and quantities derived from them, the full, possibly weighted, distribution of intensities, and the values of a histogram approximating the intensity distribution. Optionally one or more moments of the intensity distribution, values of a histogram approximating the intensity distribution, and/or other information about the intensity distribution, are found directly from the training images and/or the image being processed, without ever finding the full intensity distribution. In all these cases, the intensity distribution is optionally weighted in some way, before these quantities are found. Optionally the information on intensity distribution includes not just a single number, but a plurality of numbers, such as the values of a histogram of intensity, or two or more moments of the intensity distribution, that are matched as a vector.

It should be understood that the "organ intensity characteristics" learned from the image being processed need not include, for example, actual numbers specifying how contrast agent is used, or numbers quantitatively characterizing a degree of contrast in the image, but could include only specifying a cluster of training images with organ intensity characteristics that provide a good match to the characteristics of the image being processed, or only specifying one or more quantities derived from such a cluster of training images, for example an intensity histogram derived from the cluster.

Alternatively, data supplied with the image by a radiologist or technician who made the image is used, instead of or in addition to the contents of the image, in choosing a cluster, or a set of organ intensity characteristics, that provides a good match for the image.

Optionally, the parameters of image processing, that depend on the set of organ intensity characteristics that was matched to the image being processed, comprise information on a distribution of intensities, and/or a distribution of intensity gradients, that is expected for images with those intensity characteristics in or near the target organ, for example based on a distribution of intensities and/or a distribution of intensity gradients learned from training images in a cluster with organ intensity characteristics that provides a good match to the image being processed. Optionally, the parameters of image processing include a choice of which of two qualitatively different image processing algorithms to use. For example, as described below in 1006 of FIG. 10, a choice is optionally made of whether or not to include intensity gradients in the cost function of a region-growing algorithm for segmentation of the target organ, depending on information about the expected distribution of intensity gradients inside and at the boundary of the target organ in the image being processed.

An aspect of some embodiments of the invention concerns a method of automatically determining if a medical image has a field of view that includes abdominal organs, by first determining if the image includes at least a portion of the lungs, and segmenting the lungs if it does. It is assumed that the directions of the principle body axes in the image are already known, at least to good approximation. Automatically finding the lungs in a medical image of the trunk of the body may be relatively easy because the lungs, which contain air, generally have a much lower density than other body tissue, which will show up as a lower image intensity in the case of CT images. If the lungs are present, and the image extends at least a threshold distance below the lungs, then it is determined that the field of view of the image includes the abdomen. If the lungs are not present, and the top axial slice of the image is empty, then it is determined that the field of view of the image does not include the abdomen. If the lungs are not present, and the large leg bones can be found, then if the image extends at least a threshold distance above the large leg bones, it is determined that the field of view of the image includes the abdomen. Finding the large leg bones may be relatively easy in a medical image, because they may be the only part of the body that is that large and dense.

An aspect of some embodiments of the invention concerns a method of automatically determining which medical images of a given subject cover a given region of the body, based on the contents of the images, and selecting those images for registration. For example, a database contains multiple medical images of a subject, covering different regions of the subject's body, without metadata that indicates which images cover which regions of the body, and it is desired to register all of the images showing the abdomen, for example. An automatic determination is then made, from the contents of the images, of which images have a field of view that includes the abdomen, for example using the method described above, or any other method known in the art. Those images are then selected for registration, while the images that do not include the abdomen are not. Optionally, the method also includes automatically registering the selected images. Alternatively, the selected images are registered semi-automatically or manually.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Overview of Training, Image Processing, and Clustering

Referring now to the drawings, FIG. 1 shows a flow chart 100 illustrating an overview of a method of image processing of one or more target organs in medical images, according to an exemplary embodiment of the invention. The image processing optionally comprises segmenting the organs, and/or modifying the image, for example by anisotropic smoothing of the images in a way that preserves the sharpness of the boundaries of organs, or by adjusting the contrast of the images to make features of the organs more clearly visible. At 102, training data is optionally obtained from training images. Optionally a relatively large number of training images are used, that can provide good statistics on the appearance of the target organs in a population of patients. The training data optionally includes information on the shape and orientation of the organ, as described for example by a probabilistic atlas of the location of the organ relative to a bounding region of the organ, as well as the volume of the organ, and the distribution of intensity values and gradients for the organ and for nearby voxels outside the organ. Details on the method of obtaining training data for each target organ are given below in FIG. 4, and examples of such training data are shown in FIGS. 5A and 5B. Training data for different target organs is obtained either in parallel or consecutively, optionally using the method of FIG. 4 for each target organ of interest. As described below in the description of FIG. 4, for each target organ, the training images are optionally divided into clusters which have different organ intensity characteristics, for example due to different results of contrast agent use, or lack of contrast agent use, in the different images, or due to disease states which affect the texture of the lungs, for example. A different set of training data is then generated for each cluster, for example the target organ may have different distributions of intensity values and gradients in the training images of different clusters. Some training data which is not expected to depend on intensity characteristics, for example probabilistic atlases of the target organs, is optionally generated from all of the training images together, rather than separately from each cluster of training images.

In some embodiments of the invention, some or all of the training data on organ intensity characteristics is generated using a theoretical model, rather than from actual training images acquired from subjects. For example, a model of how contrast agent diffuses through an organ can be used to predict how different image intensity values will be distributed in an organ, depending on quantity, timing, or type of contrast agent used. A plurality of sets of organ intensity characteristics is optionally generated using the model, each set exemplifying a different appearance of the organ, based on one or more of a different level of contrast agent in the organ, a different disease state, or some other difference that affects organ intensity characteristics. The different sets of model-generated organ intensity characteristics then optionally play a similar role to the different clusters of training images acquired from subjects, each corresponding to a different set of organ intensity characteristics.

At 104, the first of the test images to be processed is received. At 106, a determination is made as to whether the test image being examined covers the part of the body that would include the target organs, for example the abdomen. Optionally, this determination is made automatically by computer, with no user intervention, for example using the method described below in FIG. 6, or the method described in U.S. Pat. No. 8,170,306 (Yu et al.), or any other known method of automatically determining the part of the body covered by the field of view of a medical image.

If the test image being examined is expected to include the target organs, then image processing is performed on the target organs in the test image, at 108. Optionally the image processing comprises segmenting the target organs, and a method of segmenting the target organs in the test image, using the training data obtained at 102, is described below in FIG. 8. When the training images have been clustered, for a given target organ, and each cluster has its own training data for that target organ, then the test image is matched to a cluster, as described below in FIG. 8, before doing the image processing for that target organ, so that the appropriate training data can be used. If model-generated sets of organ intensity characteristics are used instead of training data obtained from clusters of training images, then the test image is matched to one of the sets, optionally using the methods described below in FIG. 8.

After image processing the target organs in the test image, the method determines, at 110, if there is another test image to be examined. This is done immediately after 106, if it is determined that the image being examined at 106 is not expected to include the target organs. If there is another test image, then it is received at 112, and a determination is again made, at 106, as to whether the test image is expected to include the target organs or not. If there are no more test images to be examined, the method ends at 114. In some embodiments of the invention, 106 and 108 are performed for some or all of the different test images in parallel, rather than consecutively as shown in FIG. 1.

Figure 2:
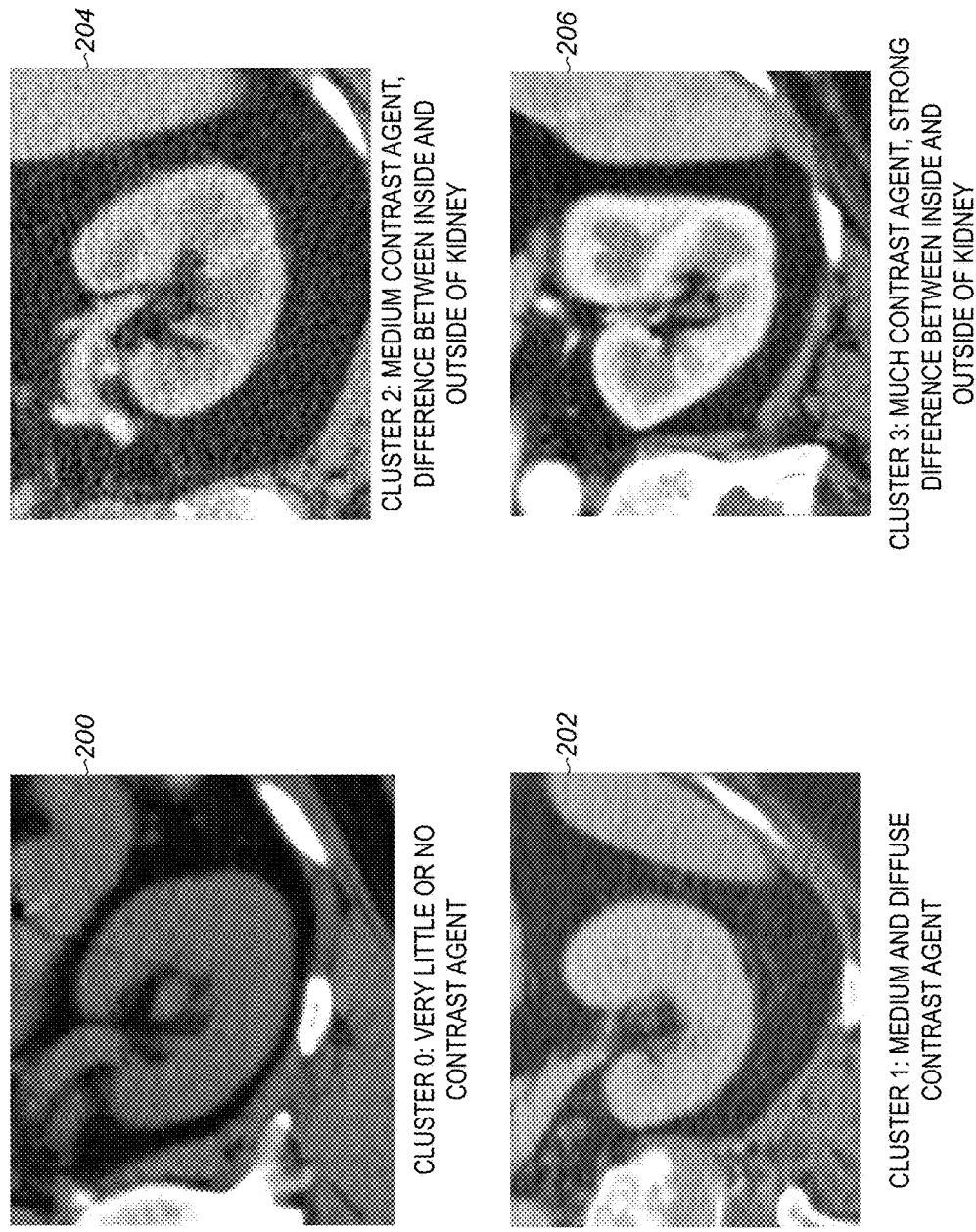
FIG. 2 shows four CT images of two-dimensional axial slices of left kidneys in different patients taken at different times, illustrating different degrees and/or timing of contrast agent use, each image belonging to a different cluster of organ intensity characteristics according to an exemplary embodiment of the invention.

FIG. 2 shows examples of training images of the same organ, the left kidney, that are assigned to different clusters for purposes of producing the training data. Each image shown in FIG. 2 is a two-dimensional axial slice of a full three-dimensional CT image covering a region around the left kidney. Image 200 is an example of an image made without contrast agent, assigned to cluster 0. Image 202 is an example of an image made with a medium amount of contrast agent in the kidney, distributed fairly evenly throughout the kidney, and is assigned to cluster 1. Image 204 is an example of an image that is also made with a medium amount of contrast agent, but with a significant difference between an inner and outer portion of the kidney, and is assigned to cluster 2. Image 206 is an example of an image made with a large amount of contrast agent, with a strong difference between the inner and outer portions of the kidney, and is assigned to cluster 3.

The different appearances of images in the different clusters can result at least from the following factors:

1) the type of contrast agent used, if any, and whether it is given orally or injected;
2) the amount of contrast agent used;
3) where the contrast agent was injected;
4) the timing between when the contrast agent was introduced, and when the image was made;
5) the rate of bloodflow of the subject, which can affect how long it takes for the contrast agent to reach the target organ, and how the contrast agent is distributed in the organ after it reaches the organ, as well as the rate of absorption of the contrast agent in the gastrointestinal tract, in the case of orally administered contrast agent, which can affect the timing and amount of contrast agent reaching the organ;
6) other differences between subjects, for example differences in the amount of blood or density of blood vessels in the target organ, or other differences in tissue characteristics, including differences caused by disease or injury, which may affect how the appearance of the tissue is affected by contrast agent;
7) differences in imaging parameters, for example x-ray energy, intensity and exposure time in the case of CT images, that affect how the image intensity is affected by contrast agent.

Figure 3:
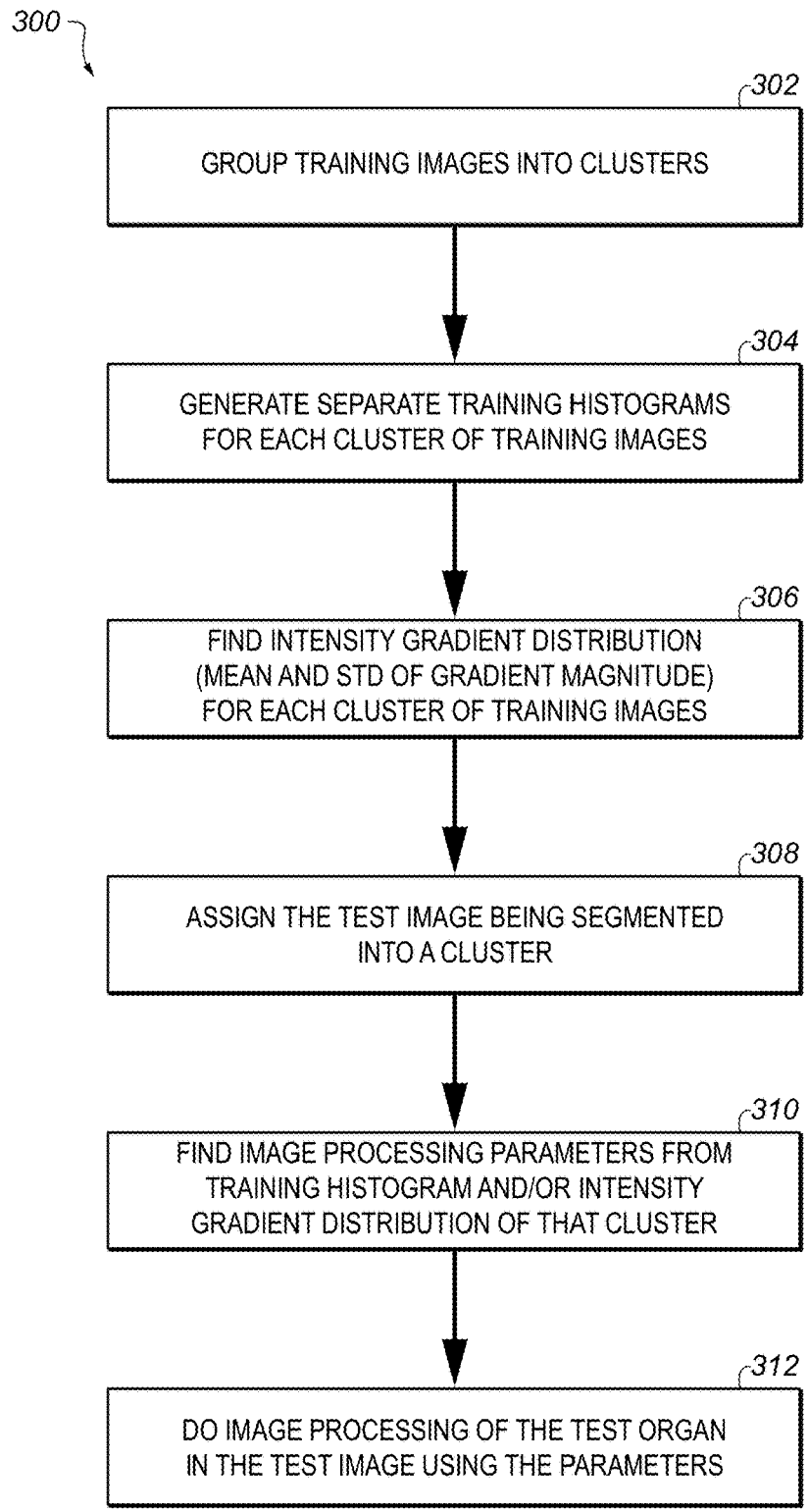
FIG. 3 is a flow chart showing different elements of a method of generating training data from training images of a target organ and using the training data to process a test image of the target organ, with the training images grouped into clusters according to organ intensity characteristics, such as the clusters illustrated in FIG. 2, and the test image assigned to one of the clusters according to its image characteristics, the image processing being done according to parameters that differ for different clusters, according to an exemplary embodiment of the invention.

FIG. 3 shows a flow chart 300, summarizing different ways in which clustering of images, based on organ intensity characteristics, is used in the method of FIG. 1, for a given target organ. At 302, the different training images that include the target organ are grouped into clusters, based on differences in their organ intensity characteristics, such as the differences shown in FIG. 2. Exemplary methods of grouping the images into clusters are described below, in 414 of FIG. 4. At 304, separate training histograms are found for each cluster of training images, with information about the distribution of intensity for voxels inside the target organ and nearby but outside the target organ. Details of how these training histograms are found are given below, in 418 and 420 of FIG. 4. At 306, information about the distribution of intensity gradients, for example a mean and a standard deviation of the magnitude of the gradient, is found, for voxels inside the target organ and for voxels at the edge of the target organ, for each cluster, as described below in 422 of FIG. 4.

At 308, when a test image has been acquired for image processing using the training data, the test image is assigned to one of the training clusters, which has organ intensity characteristics that most closely resemble those of the test image, or at least a region of the test image that includes the target organ. Details of how this is done are described below at 810 of FIG. 8. At 310, image processing parameters are found from the training histogram and/or from the information on intensity gradient distribution for the assigned cluster, and the image processing is done, using the image processing parameters, at 312.

For example, if the image processing comprises performing anisotropic smoothing on the region of the target organ in the test image, in order to reduce noise but to keep the edge of the target organ sharp, then the training data is used to obtain information, for example a mean and standard deviation, of the magnitude of the intensity gradient near the edge of the target organ. Then, for each voxel in the region of the target organ in the test image, a determination is made whether or not the intensity gradient has a value typical of the edge of the target organ. If it does, then smoothing at that voxel is done only or largely in a direction perpendicular to the direction of the gradient, which would be parallel to the edge of the target organ, while smoothing is less, or absent altogether, in a direction parallel to the direction of the gradient, which would be normal to the edge of the target organ. Even if the voxel is located in the interior of the organ, if it has a large gradient of intensity it may be located at a boundary of an internal structure inside the organ, for example a boundary between the inside and outside portions of the kidney seen in images 204 and 206 in FIG. 2, so it may still be desirable to use anisotropic smoothing to avoid blurring that boundary. If the voxel has a magnitude of gradient less than a value typical of the edge of the target organ, then it is probably located in the interior of the target organ, or outside the target organ, in a relatively uniform region, and smoothing at that voxel is optionally isotropic, optionally similar in magnitude to smoothing that is done perpendicular to the gradient for voxels with gradient typical of the edge of the target organ. Optionally there is a gradual transition in the behavior of the smoothing for the two cases, since there may be substantial overlap between values of gradient magnitude typical of the edge, and typical of the interior of the organ. Anisotropic smoothing of the image may reduce noise in the interior and exterior of the organ, while retaining all or much of the sharpness of the edge of the organ, and the sharpness of structures with sharp edges inside the organ. Optionally, anisotropic smoothing is done before segmenting the organ, since anisotropic smoothing may improve the quality of the segmentation, as described below at 1008 of FIG. 10.

If the image processing comprises changing the contrast or brightness of the target organ in the image, to make structures or tissues of interest more easily visible, then the training data for the assigned cluster is used to find a range of intensity that is of interest. Optionally this range is a range near a peak in the distribution of intensity for the organ. Alternatively, the training data includes information on an expected range of intensity for particular tissues or structures of the target organ, for example a cancerous lesion, found from training images where that tissue or structure was detected, optionally manually. Once the expected range of intensity is known, the intensity of the voxels in the image, or in the region of the target organ in the image, is transformed using a transformation function, preferably monotonic, that increases the contrast in that range of intensity, optionally while decreasing the contrast outside that range of intensity.

If the image processing comprises segmenting the target organ in the test image, then the image processing parameters may comprise a range of intensities expected for the organ, for the assigned cluster, and in particular a range of intensities expected for the organ and expected much less for voxels nearby but outside the organ. Optionally, a "rough segmentation" of the organ is then found by determining which voxels have intensities in the range expected for the organ, as described below in 818 and 820 of FIG. 8. Optionally, a more accurate segmentation is found using a region-growing algorithm, optionally starting from a seed in the rough segmentation, as described below in 822 and 824 of FIG. 8, and in more detail in FIG. 10. In this case, the image processing parameters optionally comprise a cost function for the region-growing algorithm, which depends on the intensity distribution and/or the intensity gradient distribution expected for the target organ, according to the training data for the assigned cluster, as described in FIG. 10.

Obtaining Training Data

Figure 4:
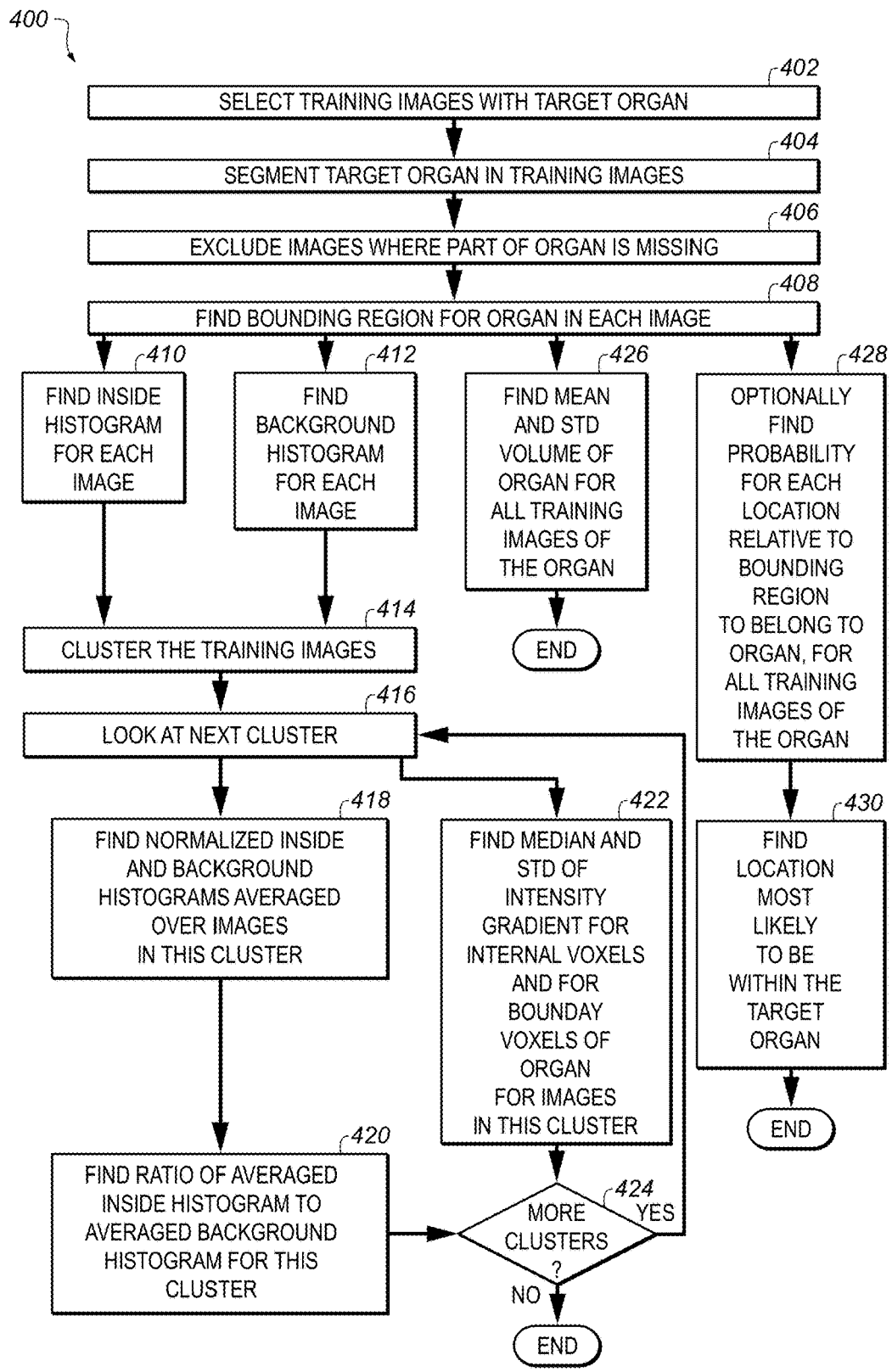
FIG. 4 is a flow chart showing a method of obtaining intensity histograms for a target organ, from training images with different organ intensity characteristics, according to the method of FIG. 1 and FIG. 3.
Figure 5A:
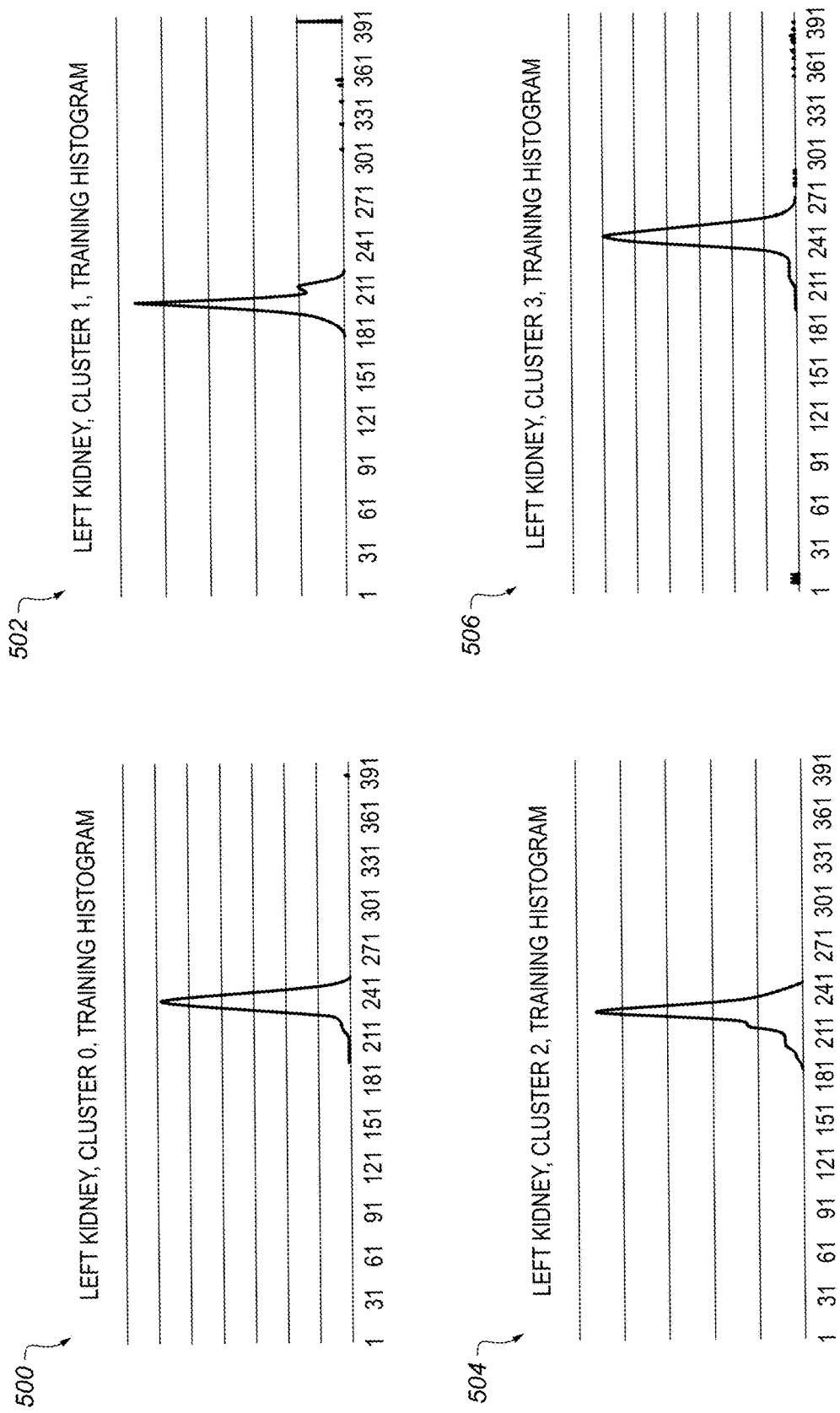
FIG. 5A shows examples of training histograms, intensity histograms based on training images of the left kidney for four different clusters corresponding to different organ intensity characteristics, prepared according to the method of FIG. 4.
Figure 5B:
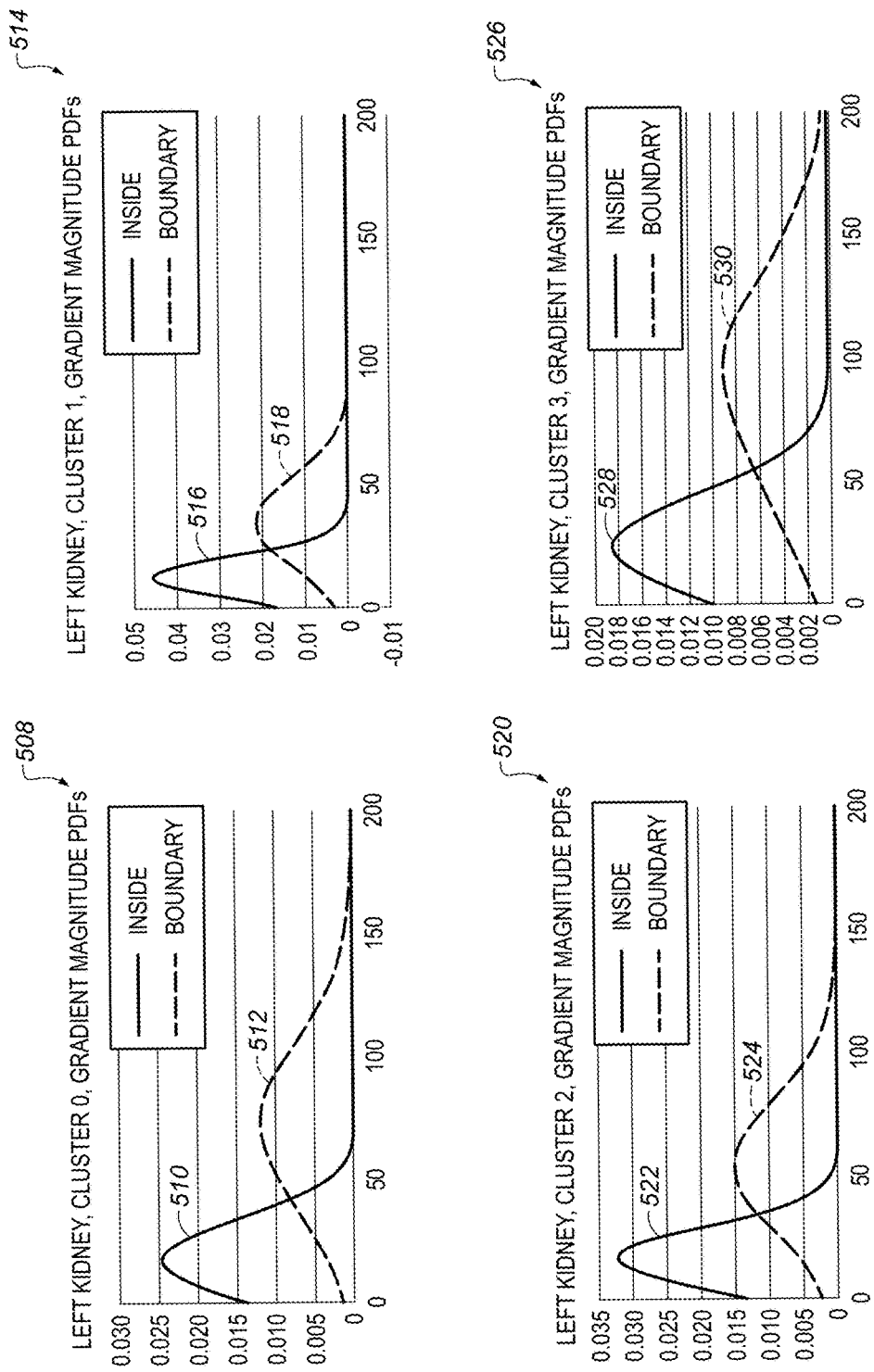
FIG. 5B shows plots of Gaussian distributions of intensity gradient, with different mean value and standard deviation corresponding to the interior and to the boundary of the left kidney for each of four clusters of different organ intensity characteristics, made from training images according to the method of FIG. 4.

FIG. 4 shows a flow chart 400, with more details on the method of obtaining training data for a particular target organ at 102 of FIG. 1, according to an exemplary embodiment of the invention. At 402, a set of training images is selected, which include the target organ. Optionally, training data for more than one target organ is obtained from the same set of training images. It is potentially advantageous if a large enough set of training images is used to provide good statistics on the appearance of the target organ in different patients, and under a range of imaging conditions, especially if the test images that the training data is to be used with are also expected to be made under such a range of imaging conditions. For example, 100 different CT images of the abdomen are used, made with a variety of different CT imaging systems, run with a range of different settings and protocols, with a range of resolutions and noise levels, ordered for a variety of reasons, from different patients, some of them exhibiting diseases that are expected to occur in test images, and that may change the appearance of affected organs. But optionally, images in which the target organ has a very abnormal appearance, due to disease or surgery, are not included among the training images, since such abnormal organs are expected to occur only rarely in test images, and including them among the training images might make the training data less useful for segmenting the great majority of test images. Optionally, some of the training images use contrast agent and some do not, with different types of contrast agent, introduced orally or intravenously or both, different amounts of contrast agent, and different timing of the image after the contrast agent was introduced, in different training images.

At 404, the target organ is segmented in each training image. Optionally, the segmentation is done manually by an expert, or semi-manually. It is advantageous for the segmentation of the target organ in the training images to be accurate, in order to obtain training data that is accurate and hence useful for later automatic segmentation of test images. At 406, training images that only include part of the target organ are excluded. Optionally that is done before the organ is segmented in training images.

At 408, a bounding region is optionally found for the target organ, in each training image. The bounding region is, for example, a rectangular box, oriented along the principle axes of the body in the medical image, that extends in each principle direction between the maximum and minimum value of the coordinate for that direction, for any voxel in the organ. Such a box is the smallest rectangular box, oriented along the principle axes, that includes all of the voxels in the organ. The bounding region is not found in order to specify the location of the target organ relative to the entire body, but in order to specify the orientation, shape and size of the organ, by finding the location of the organ relative to the bounding region. For this purpose, the bounding region need not be a rectangular box oriented along the principle axes of the body, but can be any standard shape specified by relatively few parameters, for example a rectangular box oriented in a different fixed way relative to the principle body axes, or a circular cylinder or elliptical cylinder oriented along the principle axes of the body or in some other fixed way, or an ellipsoid, or a parallelepiped with fixed angles or parameterized angles, or a prism with cross-section of specified shape or a shape specified by one or a few parameters. Using a bounding region that is a rectangular solid, oriented along the principle body axes, has the potential advantage that it is easy to define, in the case where the image consists of voxels arranged in a Cartesian coordinate system oriented along the principle body axes, as in usually true of medical images. The inventors have found that using such a bounding region produces good results, and for convenience it will be assumed in the description that follows that the bounding region is such a rectangular box. The bounding region for a target organ in a given image can then be found by finding the maximum and minimum values of each coordinate, for any voxel in the target organ. However, it should be understood that any other form of bounding region can be used instead, and it will be clear to one of skill in the art how to implement the methods described herein using a different form for the bounding region. In some embodiments of the invention, a probabilistic atlas is not generated, and in those embodiments the bounding region need not be the smallest box of some shape and orientation that includes all of the voxels of the target organ. Even in those cases, however, the bounding region optionally surrounds the target organ fairly closely, and is defined in a consistent way for different training images, so that it is meaningful to obtain statistical data about corresponding target organs in different training images.

Intensity histograms are then found for each image, at 410 and 412, in parallel, or consecutively. In the case of CT images, the intensity of a voxel is typically specified in Hounsfield units (HU). Other intensity units are used in different imaging modalities, for example in MRI images. The method has been implemented by the inventors for CT images, and will be described herein with reference to CT images, but the method could be used with other imaging modalities as well. Optionally, the images are smoothed, for example to reduce noise, using any known image smoothing algorithm, before finding the intensity histograms. However, the inventors found that, at least for the CT images that were used, better results were achieved without smoothing the images.

At 410, an inside intensity histogram is found, for each image, for the voxels inside the target organ. At 412, a background intensity histogram is found, for each image, for the voxels in the bounding region that are outside the target organ. Optionally, a histogram of the intensities of all the voxels in the bounding region is also found, for each image. Optionally, the histograms for all the training images are each normalized, for example to have an integrated value of 1, so that they can be meaningfully compared to each other, and so that histograms from different images can be meaningfully averaged together, even if the images have different resolutions and hence different numbers of voxels in a given volume.

At 414, the histograms from the different images are optionally used to sort the images into clusters representing different organ intensity characteristics, due for example to different types of contrast agent, and/or different degrees and timing of contrast agent use. Such clustering is especially useful if the test images for which the training data is intended, and the training images themselves, have a wide variety of organ intensity characteristics, which are not necessarily learned easily from data associated with the images. It should be understood that, even if the method used for sorting the training images into clusters happens to produce a cluster which only has a single training image belonging to it, it is still referred to as a "cluster." But it is potentially advantageous to use enough training images with a range of organ intensity characteristics such that each cluster will include many training images, in order to obtain training data with better statistics.

The following method has been found by the inventors to work well for sorting the training images into clusters. Alternatively, any other known method of clustering is used, including manual clustering of the training images by a human expert. In the method described below, it is not decided in advance where the divisions between the different clusters will fall, but this is decided based on the contents of the training images that are used. However, in some embodiments of the invention, it is decided in advance, based on a theoretical model, where the divisions between the clusters will fall, at least approximately. For example, based on a model of how contrast agent will be distributed in the target organ under different circumstances, it may be decided in advance that each cluster will include images that are close to the model's predictions for the appearance of the organ, for a different pre-defined manner of using contrast agent, and this may be done whether the clustering is done automatically or manually.

Optionally, the normalized inside intensity histograms are used for clustering the training images. Alternatively, a different choice of histogram is used, for example the normalized intensity histogram of all the voxels in the bounding region, for each image. Alternatively or additionally, the clustering may be based on a different measure of organ intensity characteristics, for example on a measure of texture in the organ, which depends on the fine spatial distribution of voxels of different intensity, and not just on an overall intensity histogram.

The clustering is done by treating each training histogram as a vector, with each histogram bin being treated as a single coordinate in the vector. Each such vector forms a single sample for the clustering algorithm.

K-means clustering is used, optionally with four clusters, optionally with a Bhattacharyya clustering distance measure (defined in Bhattacharyya, A., "On a measure of divergence between two statistical populations defined by their probability distributions," Bulletin of the Calcutta Mathematical Society 35: 99-109 (1943)), which is known to work well for probability functions such as those represented by these histograms, and optionally with ten random clustering re-initializations, stopping the clustering algorithm when the change in distance between iterations is below a threshold, for example $10^{-8}$. For each initialization, the input samples are optionally split into four random sets of roughly equal size, which are used to initialize the k-means. In this manner, ten potentially different clusterings of the input samples are achieved. Optionally, the clustering is selected that gives the most samples in its smallest cluster, which has the potential advantage of avoiding clusters with very few samples, representing only a few training images, which may lead to over-learning of intensity statistics. Alternatively, other methods of combining the ten results to create a final clustering are used, such as using a voting mechanism. The number of clusters, and other parameters of this k-means clustering, were chosen experimentally, by dividing 100 training studies into five exclusive divisions of 80 training and 20 test sets and finding the parameter setting that led to the best organ segmentation, of the liver, the spleen, and the left and right kidneys in the resulting test images. Visually, the four clusters correspond roughly to organs with no contrast agent, organs with very weak contrast, organs with stronger contrast, and organs with very strong contrast. In the case of the kidneys, the clustering separated kidneys with no contrast, kidneys with weak contrast approximately evenly distributed throughout, kidneys with stronger contrast and some gradient between the inner and outer regions, and kidneys with very strong contrast along the outer surface and a large gradient between the inner and outer regions. In these tests, it was visually verified that the clustering algorithm successfully separated the test organs into such visually-distinct clusters, and also that new previously unseen images of organs were correctly mapped into the expected cluster, based on their visual appearance.

For each cluster, an average or representative histogram is found from intensity histograms for the training images in that cluster, and saved as part of the training data. For example, the average or representative histogram is optionally the mean of the normalized intensity histograms of the voxels in the bounding region for all the training images in that cluster. Alternatively, the average or representative histogram is the mean of the normalized inside histograms of the training images in that cluster, or is based on some combination of inside histograms and histograms of the whole bounding region. This average or representative histogram is sometimes referred to as the "cluster center" and is used to assign test images to one of the clusters, as described below in 810 of FIG. 8.

Alternatively, the training images are not clustered, but training images with different organ intensity characteristics are lumped together. Alternatively, only images with similar organ intensity characteristics are chosen for use as training images, and optionally the resulting training data is only used for test images with organ intensity characteristics similar to that of the training images, so there is no reason to cluster the images. If clustering is not done, then all the training images may be considered to belong to a single cluster, in the description that follows.

In the description that follows, the different clusters are processed sequentially. Alternatively, all or some clusters are processed in parallel.

At 416, one of the clusters is examined. Two types of data are generated from the training images in the cluster, at 418 and 420, and at 422, in parallel, or consecutively in any order. At 418, inside and background histograms are found, averaged over all the training images in the cluster. The ratio of the inside histogram to the background histogram is then found at 420, to produce a "training histogram" for that organ, which indicates for which relatively narrow ranges of intensity a voxel in the bounding region is relatively most likely to be in the target organ, rather than outside the target organ. Optionally, the averaged inside and background histograms are normalized before taking their ratio, but this is not expected to be very important because only the shape of the training histogram is used, not its absolute magnitude. Optionally, any reasonably smooth monotonic function of the training histogram is used instead of the training histogram, since it is generally the locations and widths of the peaks that matter when the training histogram is used to segment test images, as will be clear from the description of the method of segmenting test images in FIG. 8, below.

FIG. 5A shows plots 500, 502, 504, and 506, showing an example of a training histogram for the left kidney, for each of four clusters, designated cluster 0, cluster 1, cluster 2, and cluster 3. Each of these clusters represents a group of training images of the left kidney with different image characteristics, with typical examples of training images for each cluster shown in FIG. 2. As noted above in the description of FIG. 2, cluster 0 consists of images made with little or no contrast agent in the kidney, cluster 1 consists of images made with a medium amount of contrast agent distributed fairly evenly throughout the kidney, cluster 2 consists of images made with a medium amount of contrast agent, with a significant difference in concentration between the inner and outer portions of the kidney, and cluster 3 consists of images made with a large amount of contrast agent, with a strong difference between the inner and outer portions of the kidney. The horizontal axis of each plot shows the bin number for the intensity, increasing from left (lower intensity) to right (higher intensity). The bins are each 5 HU wide, and range from −990 HU to +1000 HU, while the vertical axis is arbitrary. As is typical for the organs that have been tested by the inventors, there is a dominant narrow peak centered at one value of intensity. There are also smaller peaks to the side of the dominant peak, corresponding to different portions of the kidney with different intensities, which become more separated from the dominant peak as the amount of contrast agent increases, going from plot 200 to plot 206. Knowing what values of intensity are relatively most likely to occur inside the kidney rather than within the bounding region but outside the kidney, for a given cluster, can be useful in segmenting the kidney in other images that are assigned to that cluster based on their organ intensity characteristics.

At 422 in FIG. 4, the median and standard deviation of the magnitude of the intensity gradient are optionally found, for internal voxels of the target organ, and for voxels at the boundary of the target organ, for all images in this cluster. Alternatively, the mean, mode, or another type of average value is used instead of the median, but the inventors have found that using the median works well because it is insensitive to outliers. Optionally, the magnitude of the full three-dimensional intensity gradient is used. Alternatively, for example to save computation time, only the magnitude of the intensity gradient within two-dimensional slices of the image is used, for example within axial slices, or within coronal slices, or within sagittal slices. Optionally, the distribution of the intensity gradient is normalized for each image, before averaging the distribution functions for the different images and finding the median and standard deviation of the averaged distribution function. Such normalizing will allow different images to have the same weight in finding the averaged distribution, even if they have very different resolutions and hence very different numbers of voxels in the target organ. Alternatively, the full distribution function of intensity gradients in the interior and on the boundary of the organ are kept as part of the training data, instead of or in addition to the median and standard deviation, and/or other moments of the distribution function are kept. Alternatively, information on the intensity gradients is not found at all, and is not used in segmenting the organ in test images. However, the inventors have found that using the median and standard deviation of the intensity gradient, for the interior voxels and boundary voxels, is often useful for determining the exact boundary of the target organ in a test image, since many organs have much sharper intensity gradients at the boundary than in the interior.

FIG. 5B shows plots of Gaussian curves showing the median and standard deviation of intensity gradient for voxels inside the left kidney, and on the boundary of the left kidney, for each of clusters 0, 1, 2, and 3 (defined above in the description of FIG. 2). Plot 508 shows curve 510 for voxels inside the kidney, and curve 512 for voxels on the boundary of the kidney, for training images in cluster 0. Plot 514 shows curve 516 for voxels inside the kidney, and curve 518 for voxels on the boundary of the kidney, for training images in cluster 1. Plot 520 shows curve 522 for voxels inside the kidney, and curve 524 for voxels on the boundary of the kidney, for training images in cluster 2. Plot 526 shows curve 528 for voxels inside the kidney, and curve 530 for voxels on the boundary of the kidney, for training images in cluster 3. The intensity gradient is given in HU per millimeter. Only the two-dimensional intensity gradient within axial slices was used to find the curves. The voxels on the boundary have much greater median and standard deviation of intensity gradient, than the voxels in the interior, and this fact can be used in segmenting a target organ using a region-growing algorithm, to indicate when the boundary may have been reached. The mean and standard deviation are different in different clusters, especially in cluster 3, representing images with large amounts of contrast agent, which has much higher mean and standard deviation of intensity gradient, both inside and at the boundary of the left kidney, so it is information on the distribution of intensity gradient is much more useful if the training images are divided into clusters, with separate information on distribution of intensity gradient provided for each cluster.

At 424 in FIG. 4, if there are more clusters remaining, then the next cluster is examined at 416. If there are no more clusters, then the procedure ends.

Two other types of training data are optionally found, at 426, and at 428 and 430, in parallel with the training data found at 410 to 424. Alternatively, the training data is found at 426 and/or at 428 and 430 consecutively with the training data found at 410-424, in any order.

At 426, the mean and standard deviation are optionally found for the volume of the target organ, for the training images being used for this organ.

At 428, the probability is found, for each location relative to the bounding region, that the location is in the target organ. The set of probabilities for a given organ is referred to as a "probabilistic atlas" for that organ. In order to meaningfully compare bounding regions that in general have different dimensions in different images, the bounding region in each image is mapped into the probabilistic atlas, for example by linearly scaling the different dimensions of the bounding region, using scaling factors that may be different for different directions and different images. For example, if the bounding region is a rectangular box, then the probabilistic atlas is optionally a cube of width 1, with each coordinate ranging from 0 to 1, and the width of the rectangular box in each principle direction, in each image, is optionally normalized to 1 when it is mapped to the probabilistic atlas. In this way, each location in the probabilistic atlas maps to a location in the bounding region in each image, and it is possible to find the probability that that location in each image falls within the target organ in that image. Alternatively, a different mapping is used between the bounding regions of the different images and probabilistic atlas, for example a center point of the bounding region in each image maps to a location at the center of the probabilistic atlas, and other points in the bounding region of a given image map to a point in the probabilistic atlas that is displaced from the center point by the same distance in each principle body direction.

In practice, the probability is only found for a discrete set of locations in the probabilistic atlas, which may be considered voxels of the probabilistic atlas, for example 100 voxels of uniform size across the width of the probabilistic atlas in each principle direction. In general, the different images may have different numbers of voxels in a given direction across the bounding region, and any known interpolation scheme, for example closest neighbor interpolation, is used to specify whether or not a location in a given image that maps to a given voxel in the probabilistic atlas is within the organ in that image, as opposed to being outside the organ and in the background. The probability for each voxel in the atlas is then defined, for example, as the number of training images for which the corresponding location is within the organ, divided by the total number of training images that were used for this organ. Optionally, the distribution of probabilities in the probabilistic atlas is smoothed, or otherwise processed, before using it.

At 430, using the distribution of probabilities that was found in 428, a location is optionally found in the probabilistic atlas that is deemed most likely to be within the target organ. If there is only a single location for which the probability has a maximum value, then that location is chosen. More often, there is an extended range of locations for which the probability is at its maximum value, usually 100%. In that case, the location is optionally chosen to be deep within that extended range of locations, for example at a point furthest from the boundary of the extended range of locations. Optionally, distance from the boundary is defined not in the space of the probabilistic atlas, but takes into account the ratio of scaling factors in the mapping from the images to the probabilistic atlas for the different principle directions. Although this ratio differs slightly for different images, an average value is optionally used, for purposes of defining distance from the boundary.

An example of a probabilistic atlas, for the spleen, is shown in FIG. 5B and described in provisional U.S. Ser. No. 62/144,552, titled "Organ Detection and Segmentation," filed on Apr. 8, 2015, incorporated herein in its entirety.

Automatically Determining if Field of View Includes Abdomen

Figure 6:
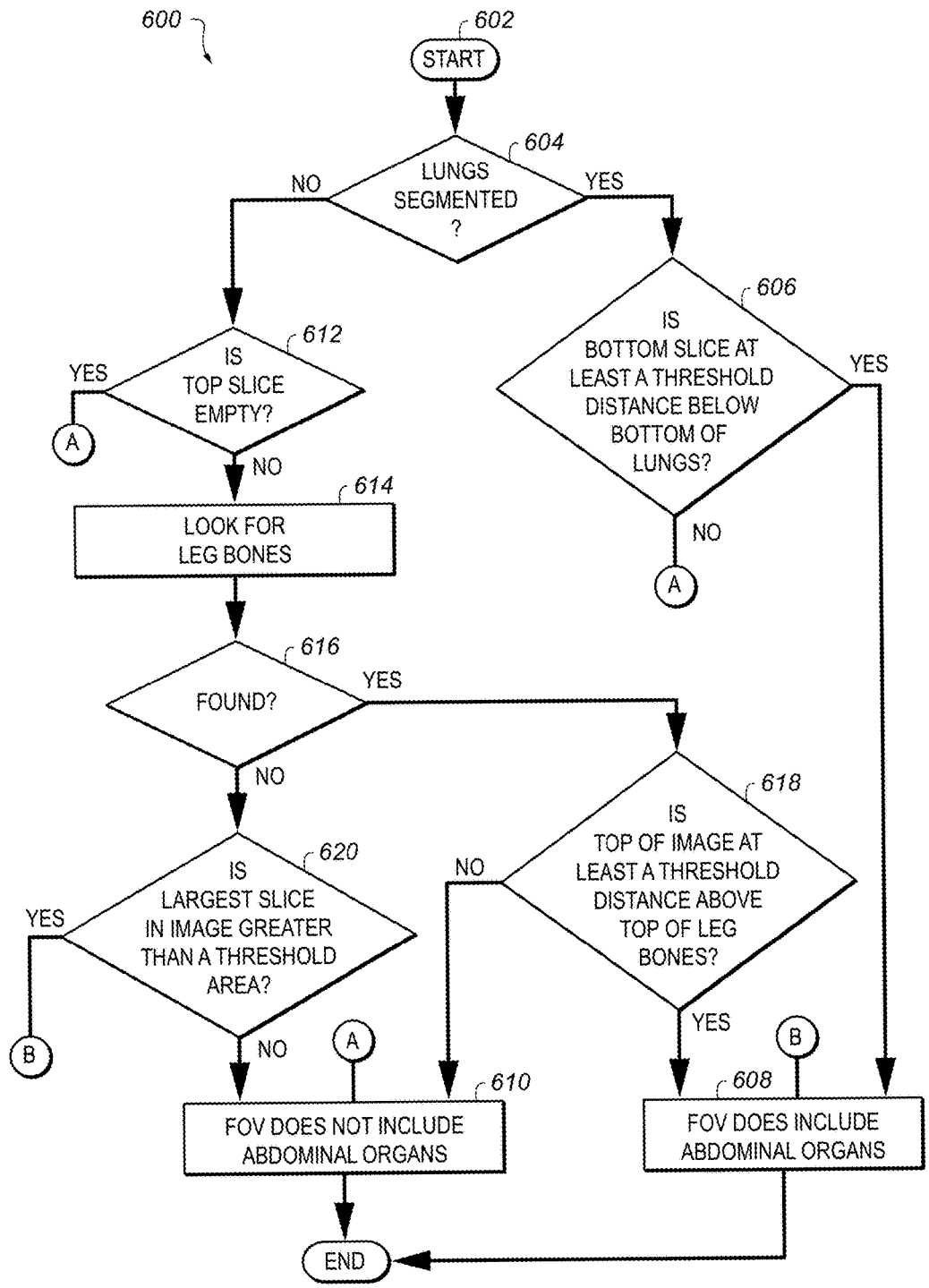
FIG. 6 shows a flow chart for a method of automatically selecting medical images that have a field of view that includes abdominal organs, suitable for use in the method of FIG. 1, according to an exemplary embodiment of the invention.

FIG. 6 shows a flow chart 600, for an exemplary method of automatically determining whether the field of view of a medical image includes target organs in the abdomen, according to an embodiment of the invention. The method of flow chart 600 is suitable, for example, for determining, at 106 in FIG. 1, whether or not target organs are in the field of view of the test image, if the target organs are located in the abdomen. The full method described below will decide, for any image that includes at least part of the body, whether the field of view of the image includes all or most of the abdomen. Optionally, only some of the elements of the method are used, in which case the method may not make a decision in all cases, but it may still make a decision in some cases, depending on which parts of the body are included in the fields of view of the images examined.

The method starts at 602. It is assumed that the orientation of the principal axes of the body in the image is known, either because this information is included with the image when it is created, or because the principle axes were later identified in the image automatically or manually. It is also assumed that it is known which voxels of the image are in the body and which are not, for example because a previous automated or manual image processing operation has determined that information, for example using simple thresholding and morphology, or any other method known in the art. In this description, "up," "above" and "top" will refer to the direction toward the head, and "down," "below" and "bottom" will refer to the direction toward the feet, regardless of the orientation of the subject when the image was acquired, and regardless of the orientation of any display of the image. At 604, an attempt is made to segment the lungs in the image. Segmenting the lungs may be relatively easy, because they contain air, and, together with the trachea, they generally have substantially lower density than any other organ. If the lungs have been successfully segmented, then at 606, a determination is made as to whether the bottom slice of the image is at least a first threshold distance below the bottom of the lungs. The first threshold distance is, for example, between 30 cm and 40 cm, for example 30 cm, 32 cm, 34 cm, 35 cm, 36 cm, 38 cm, or 40 cm, or is less than 30 cm or more than 40 cm. A smaller or larger first threshold distance is optionally used for an unusually short subject, including a subject who is a child, or an unusually tall subject, with the first threshold distance optionally depending on the height and age of the subject. The first threshold distance is also optionally made smaller or larger depending on where in the abdomen the target organs of interest are located. For example, if the target organs of interest are all in an upper part of the abdomen, relatively close to the lungs, then a smaller first threshold distance is optionally used than if at least one of the target organs extends to a lower part of the abdomen, relatively far below the lungs. If the bottom slice of the image is at least the threshold distance below the bottom of the lungs, then at 608, it is decided that the field of view of the image does include abdominal organs, and the procedure ends. If the bottom slide of the image is not at least the threshold distance below the bottom of the lungs, then it is decided at 610 that the field of view of the image does not include the abdominal organs, at least not completely, and the procedure ends.

If the lungs cannot be segmented at 604, then, at 612, it is determined if the top slice is empty of any voxels that are in the body. If the top slice is empty, then the field of view of the image must include only the head, and possibly the neck and shoulders, and at 610 it is decided that the field of view does not include the abdominal organs. If the top slice is not empty, then at 614, an attempt is made to segment the leg bones. An exemplary method of segmenting the leg bones is described below in FIG. 7.

At 616 a determination is made as to whether the leg bones were found. If the leg bones were found, then at 618 a determination is made whether the top of the image is at least a second threshold distance above the top of the leg bones. If the top of the image is at least the second threshold distance above the top of the leg bones, then at 608 it is determined that the field of view does include the abdominal organs. If the top of the image is not at least the second threshold distance above the top of the leg bones, then at 610 it is determined that the field of view does not include the abdominal organs, at least not completely. The second threshold distance is optionally between 28 cm and 38 cm, for example 28 cm, or 30 cm, or 32 cm, or 33 cm, or 34 cm, or 36 cm, or 38 cm, or is less than 28 cm, or more than 38 cm. Optionally, as for the first threshold distance, a smaller or larger value is used for the second threshold distance if the subject is unusually short, or is a child, or is unusually tall, with the second threshold distance depending on the height and age of the subject. Also, as with the first threshold distance, the second threshold distance is optionally greater or smaller depending on where in the abdomen the target organs of interest are located. For example, if the target organs of interest are all in the lower abdomen, not extending too far above the top of the leg bones, then the second threshold distance is optionally smaller than if at least one of the target organs is located higher up in the abdomen, extending further from the top of the large leg bones.

If it is determined at 616 that the leg bones were not found, then, since the lungs were also not found, the image must be limited to the head, neck and shoulders, or it must be limited to a region above the leg bones and below the lungs, which would include the abdominal organs, at least in part. To distinguish between these two cases, at 620 a determination is made whether the axial slice in the image with the largest area of voxels that lie within the subject's body has an area of voxels within the body that is greater or less than a first threshold area. The first threshold area is optionally between 250 and 400 cm². For example, the threshold area is 250, or 275, or 300, or 325, or 350, or 375, or 400 cm², or less than 250 or more than 400 cm². Optionally, the threshold area is smaller for smaller people, including children, and bigger for bigger people. If the area of voxels within the body for that axial slice is less than the threshold area, then the image is assumed to cover the head, neck, and/or shoulders, since if it covered the abdomen then the greatest area within the body for any axial slice would be greater than the threshold area, and in this case, a determination is made at 610 that the field of view of the image does not include the abdominal organs. If the greatest area within the body for any axial slice is greater than the threshold area, then it is determined at 608 that the field of view of the image does include the abdominal organs.

Figure 7:
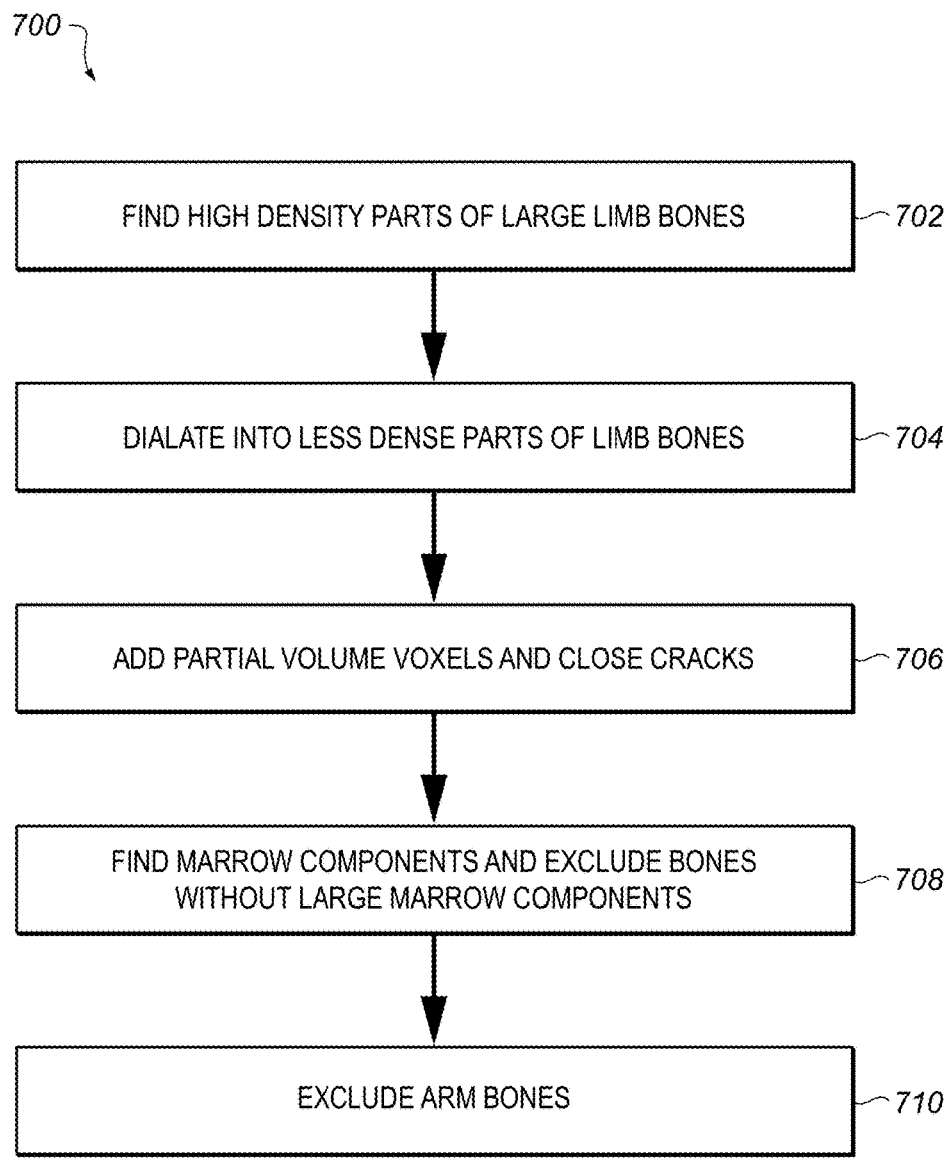
FIG. 7 is a flow chart showing further details of finding large leg bones according to the method of FIG. 6.

FIG. 7 shows a flow chart 700 that shows further details of how an attempt is made to find the leg bones in 614 of FIG. 6. At 702 a mask is created of the high density parts of the large limb bones. First, a mask is created that includes all voxels in the body with image intensity (which corresponds to density in a CT image) above a first intensity threshold, for example above 900 HU in the case of a CT image. Alternatively, the first intensity threshold is 600 HU, or 700 HU, or 800 HU, or 1000 HU, or 1100 HU, or 1200 HU, or a higher, lower, or intermediate value. This high density bone mask in general includes several disconnected components. For each component, the volume, the eigenvalues of its shape, and the orientation of its longest eigenvector is found, and only components above a threshold volume, sufficiently long and thin, and oriented with their long direction sufficiently close to the z-axis (the head-to-foot direction of the body) are kept. For example, components are kept only if their volume is greater than 5000 cm³, oriented with their long direction within 45 degrees of the z-axis, and with a major-to-middle eigenvalue ratio of at least 10, and a middle-to-minor eigenvalue ratio of at most 5, at kept. Alternatively, the volume threshold is 2500, 3000, 3500, 4000, 4500, 5500, 6000, 7000, or 8000 cm³, or a higher, lower, or intermediate value. Alternatively, the angle of orientation to the z-axis has to be less than 20 degrees, or 25 degrees, or 30 degrees, or 35 degrees, or 40 degrees, or 50 degrees, or 55 degrees, or 60 degrees, or a greater, smaller, or intermediate value, in order for the component to be kept. Alternatively, the major-to-middle eigenvalue ratio has to be at least 5, or at least 6, or at least 7, or at least 8, or at least 9, or at least 11, or at least 12, or at least 14, or at least 16, or at least 20, or a greater, smaller, or intermediate value. Alternatively, the middle-to-low eigenvalue ratio has to be at most 2, or at most 3, or at most 4, or at most 6, or at most 8, or a lower, higher, or intermediate value. The remaining components of the mask include only the high density parts of large limb bones.

At 704, the components of this high density limb bone mask are optionally dilated into less dense parts of the limb bones, but only into voxels that have intensity greater than a second intensity threshold, lower than the first intensity threshold. The dilation is, for example, 5 mm. Alternatively, the dilation is 2 mm, or 3 mm, or 4 mm, or 6 mm, or 8 mm, or 10 mm, or a lower, higher, or intermediate value. The second intensity threshold is, for example, 550 HU. Alternatively, the second intensity threshold is 300 HU, or 350 HU, or 400 HU, or 450 HU, or 500 HU, or 600 HU, or 650 HU, or 700 HU, or 800 HU, or a lower, higher, or intermediate value. The resulting large limb bone mask includes both the higher and lower density parts of the large limb bones.

At 706, the components of the medium density bone mask are further dilated, but only into voxels that have intensity greater than a third intensity threshold, lower than the second intensity threshold. This dilation is, for example, 2 mm. Alternatively, it is 0.5 mm, or 1 mm, or 1.5 mm, or 2.5 mm, or 3 mm, or 4 mm. The third intensity threshold is, for example, 150 HU, or 50 HU, or 100 HU, or 200 HU, or 250 HU, or 300 HU, or 400 HU, or a smaller, larger, or intermediate value. This dilation adds partial volume voxels, and cracks, to the large limb bone mask.

At 708, marrow components are found, and bones (components of the large limb bone mask) without large marrow components are excluded from the large limb bone mask. The large marrow components are optionally defined as sufficiently large cavities, not part of the large limb bone mask themselves, in any two-dimensional slice of the image, that are completely surrounded, in that slice, by voxels that do belong to the large limb bone mask. Optionally, only two-dimensional slices that are in one of the principle planes of the image (the xy plane, the yz plane, or the xz plane) are considered, where the x, y, and z axes are the principal axes of the body. Optionally, only axial slices (slices in the xy plane) are considered. Optionally, to be considered a large marrow component, the connected volume of cavities in a given bone has to be greater than a marrow threshold volume of 12,000 mm³. Alternatively, the volume has to be greater than 5000, or 6000, or 7000, or 8000, or 9000, or 10,000, or 11,000, or 13,000, or 14,000, or 16,000, or 18,000, or 20,000, or 24,000 mm³, or a smaller, larger, or intermediate value.

At 710, arm bones are excluded from the large limb bone mask. First, for each remaining component in the large limb bone mask, the middle axial slice of the component is examined for voxels, not in the large limb bone mask, with intensity above a fourth intensity threshold. The fourth intensity threshold is, for example, 400 HU. Alternatively, the fourth intensity threshold is 250 HU, or 300 HU, or 350 HU, or 450 HU, or 500 HU, or 550 HU, or 600 HU, or a smaller, larger, or intermediate value. If the large limb bone component is an arm bone, then it is expected that either chest bones or head bones will be found in its middle slice, depending on whether the arm is being held by the side of the body or above the head, and the fourth intensity threshold is optionally low enough so that voxels will be found that belong to bones in the chest and the head, but not so low that the voxels found will include large areas of non-bone tissue, and higher than the third intensity threshold. Any voxels found in the middle slice, outside the large limb bone mask, are dilated, only into voxels that have intensity above the third intensity threshold, for example by 20 mm. Alternatively, this dilation is by 10 mm, or 15 mm, or 25 mm, or 30 mm. If a connected component of the dilated voxels has area less than a second threshold area, then it may be a blood vessel in the thigh, and these components of the dilated voxels are excluded. The second threshold area is, for example, 100 mm². Alternatively, the second threshold area is 50, or 75, or 125, or 150, or 200 mm², or a smaller, larger, or intermediate value. If there remain any components of the dilated voxels that are greater than the second threshold area, then these components are considered to be chest or head bones, and the large limb bone component is considered to be an arm bone, and is excluded from the large limb bone mask. The remaining components of the large limb bone mask are the large leg bones.

Segmentation of Target Organs

Figure 8:
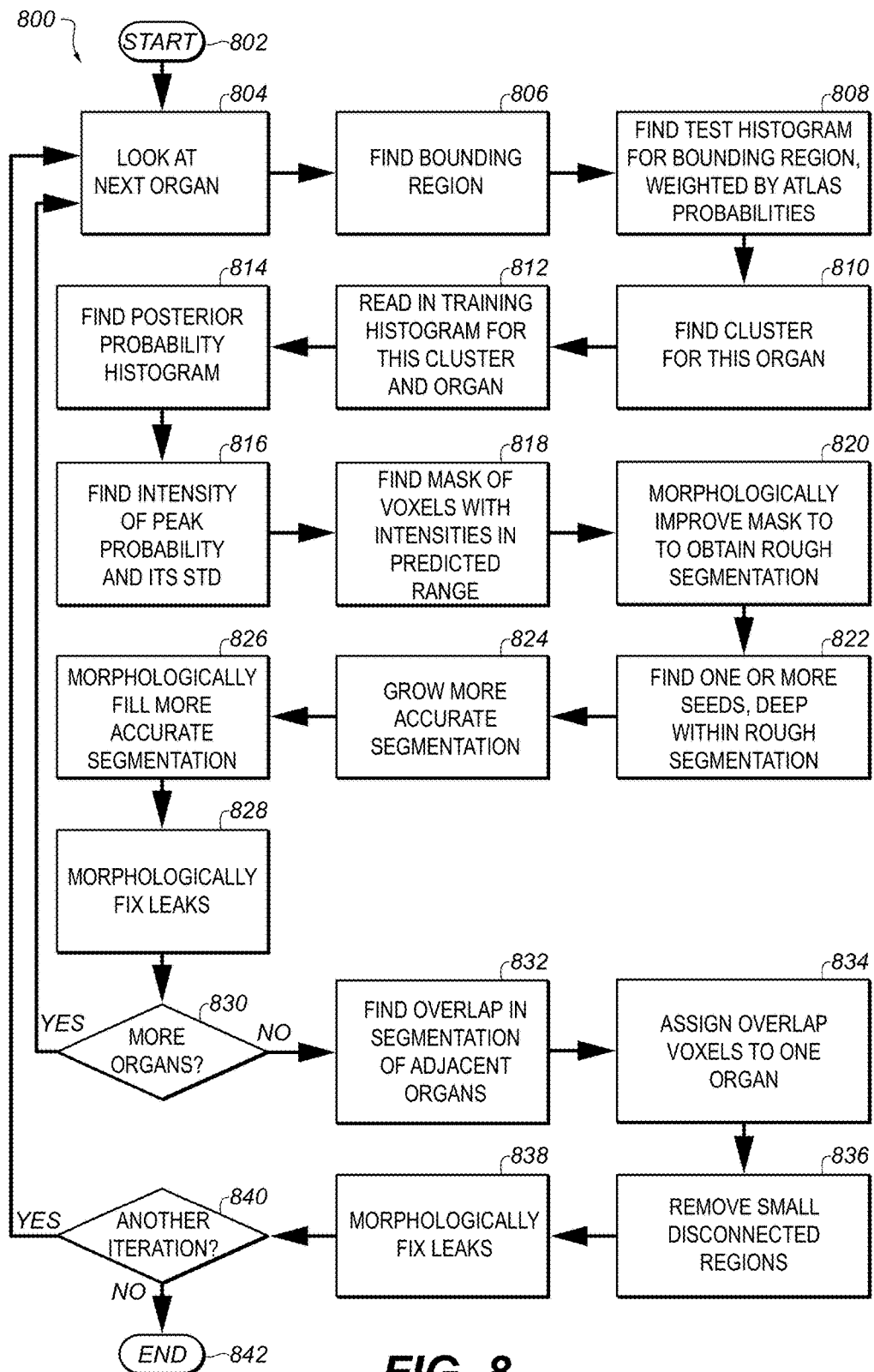
FIG. 8 is a flow chart for a method of segmenting an organ using training data clustered according to organ intensity characteristics, suitable for use in the method of FIG. 1, according to an exemplary embodiment of the invention.

FIG. 8 shows a flow chart 800 for a method of segmenting one or more target organs in a test image, according to an exemplary embodiment of the invention, using training data that was generated by the method of FIG. 4, or similar data that was generated by any other method, for example by a theoretical model. The procedure starts at 802, when a test image is selected. At 804, the first target organ is selected for segmentation. Although FIG. 8 shows different target organs being segmented consecutively, in a loop going from 804 to 830, some or all of the different target organs are optionally segmented in parallel, instead.

The bounding region for the target organ is found at 806. Optionally, any known method is used for finding a preliminary segmentation for the target organ, and the bounding region is defined the same way as in the training images, for example as the smallest rectangular box, with principle axes aligned with the principle body axes, that includes all of the target organ according to the preliminary segmentation. Alternatively, a method is used that finds the bounding region of the organ in the image, even without first finding a preliminary segmentation of the organ. Known methods of finding a preliminary segmentation or a bounding region of a target organ in a medical image include:

1) Learning-based methods, based on knowledge encoded during an off-line training process, often involving manual or semi-manual ground-truth segmentations of training images, for example involving the locations of organs relative to a bounding box that may include the entire abdomen, or the entire body. Examples of such methods are described by Xiangrong Zhou, et al, "Automatic localization of solid organs on 3D CT images by a collaborative majority voting decision based on ensemble learning," *Computerized Medical Imaging and Graphics,* 36 (2012), 304-313, and by Antonio Criminisi, et al, "Regression forests for efficient anatomy detection and localization in computed tomography scans," *Med. Image Anal.* (2013), available from <http://dx.doi.org/10.1016/j.media.2013.01.001>.

2) Registration-based methods, in which a medical image is registered to an image in an atlas that covers a large field of view, such as the entire abdomen, or the entire body. An example of such a method is described in Hyunjin Park, et al, "Construction of an Abdominal Probabilistic Atlas and its Application in Segmentation," *IEEE Transactions on Medical Imaging,* Vol. 22, No. 4, April 2003, 483-492.

3) Any other known method of segmenting an organ in medical image, whose accuracy is insufficient, can be used to find a preliminary segmentation in order to find a bounding region in 606. For example, a method using neural networks and fuzzy rules for this purpose is described in Chien-Cheng Lee, et al, "Identifying multiple abdominal organs from CT image series using a multimodule contextual neural network and spatial fuzzy rules," *IEEE Transactions on Information Technology in Biomedicine,* Vol. 7, No. 3, September 2003, 208-217.

Alternatively, these or other known methods are adapted to give a bounding region for the target organ directly, without ever finding a preliminary segmentation of the target organ.

At 808 an intensity histogram is found for the voxels in the bounding region in the test image, with the contribution from each voxel optionally weighted by a weighting factor that depends on the probability of the corresponding location in the probabilistic atlas. The location in the probabilistic atlas that corresponds to a given voxel in the test image is optionally defined, for example, by a linear mapping from the bounding region in the test image to the probabilistic atlas, with possibly different scaling factors in each principal direction, and the probability of the location is optionally found from the probabilities of the voxels in the probabilistic atlas by any known interpolation scheme, for example using the probability of the nearest voxel in the atlas. For example, the weighting factor is the probability, or is proportional to the probability. Alternatively, the weighting factor is a nonlinear function of the probability, for example a function proportional to the square of the probability, or another power of the probability. Optionally the weighting function is an increasing function of the probability, so that voxels with greater probability of belonging to the target organ are given greater weight. Optionally, the distribution of probability in the probabilistic atlas is smoothed or otherwise processed, before using it to find the weighting factor. The resulting test histogram represents the distribution of voxel intensities in the organ and its vicinity. Optionally, the test image is smoothed slightly before calculating the test histogram, although the inventors have found that better results are generally obtained without smoothing. If the training images are smoothed before calculating the training histogram, then optionally the test image is smoothed in the same way, before calculating the test histogram. Optionally, the range and bin size of intensities for the test histogram is the same as the range and bin size of intensities for the training histogram, for example, in the case of CT images, a range of −990 to +1000 HU, with a bin size of 5 HU has been found by the inventors to work well. Optionally, the test histogram is normalized to its peak value, so that it can have values ranging between 0 and 1.

In some embodiments of the invention, instead of finding the full test histogram at 808, only some characteristics of the weighted distribution of voxel intensities in the bounding region of the test image are found. For example, optionally the peak value and width of local peaks in the weighted distribution of voxel intensities are found directly from the intensity values of the voxels, without ever finding the full test histogram. For example, the weighted number of voxels is found within each of a several relatively coarse bins of intensity, and within each bin that has a great enough weighted number of voxels, the weighted mean and standard deviation of intensity is found. In this case, the information on the height and width of local peaks is used instead of the full test histogram, in what follows.

In some embodiments of the invention, instead of or in addition to using the distribution of intensities in segmenting the test organ, a different organ intensity characteristic, for example texture, is used. Texture in an image can be quantitatively characterized, for example, using the methods described by Calvin C. Gotlieb and Herbert E. Kreyszig, "Texture Descriptors Based On Co-occurrence Matrices," *Computer Vision, Graphics, and Image Processing* 51, 70-86 (1990). Quantitative methods of characterizing texture specifically in medical images, and the use of texture to distinguish normal from diseased tissue, are described for example by Wang et al, "Studies On Tissue Characterization by Texture Analysis with Co-occurrence Matrix Method Using Ultrasonography and CT Imaging," *J. Med. Ultrasonics* 29, 211-223 (2002). In the following description of FIG. 8, the segmentation method is described for the case where a distribution of intensities is used to segment the target organ, but it should be understood that distributions of other intensity characteristics, and quantities derived from them such as moments of those distributions, can be used instead or in addition.

At 810, if the training data includes separate training histograms for different clusters of training images having different organ intensity characteristics, the test histogram found in 808, or other information about the weighted distribution of voxel intensities in the bounding region, such as mean value or standard deviation, is optionally used to match the test image, for purposes of segmenting this target organ, to one of the sets of organ intensity characteristics that is similar to those of the target organ in the test image, based for example on a cluster of training images with those organ intensity characteristics. Alternatively a different kind of test histogram is used, for example an unweighted intensity histogram of the bounding region in the test image. In the case where the sets of organ intensity characteristics are based on different clusters of the training images, the test image is matched to a cluster, for example, by comparing the test histogram to the average or representative intensity histogram found for each cluster, as described above at 414 of FIG. 4, and determining for which cluster the average or representative intensity histogram is closest to the test histogram, optionally using the same distance measure used at 414 in FIG. 4 for sorting the training images into clusters, for example, the Bhattacharyya distance, as a measure of distance between the histograms, or using any other distance measure. The test image is then matched to that cluster. Optionally, the test histograms and the average or representative histograms of the clusters are defined in a way that they would be expected to be similar, if the test image has similar organ intensity characteristics to the training images of a cluster. For example, if the test histogram is an unweighted histogram of the bounding region of the test image, then the average or representative histogram of a cluster is optionally based on intensity histograms of the entire bounding region. While if the test histogram is an atlas-weighted histogram of the bounding region of the test image, then the average or representative histogram of a cluster is optionally based on inside histograms, or on a combination of inside histograms and histograms of the entire bounding region. In this way, the test image, for purposes of segmenting this target organ, will be matched to a cluster of training images for which the distribution of intensities within the organ and its vicinity is similar to the distribution of intensities in the bounding region found for the target organ in the test image. The training data for that cluster may then provide useful information on the expected distribution of intensities and gradients of the test organ, and its background voxels, in the test image.

If the different sets of organ intensity characteristics are not based on clusters of training images, but are generated in another way, for example from a model, the method of matching the test image to one of the sets is similar to what has been described. For example, each set of organ intensity characteristics may have its own representative intensity histogram, weighted or unweighted, but the representative intensity histograms are not generated from clusters of training images, but in another way, for example from a model. A distance measure is chosen, to compare the representative intensity histograms to a corresponding test histogram, defined in a way analogous to the representative intensity histograms of the sets of organ intensity characteristics, so that it makes sense to compare them. The test image is then optionally matched to a set of organ intensity characteristics for which the distance is smallest. In some embodiments of the invention, for example if there are a continuum of sets of organ intensity characteristics, each set corresponding to a linear combination of a rather large number of basis sets of organ intensity characteristics, then it might not be practical to find the single set with a representative intensity histogram which is the minimum distance from the test histogram. In this case, instead of finding the set with the absolute minimum distance, a method such as the simplex method is optionally used to find a set with an approximate minimum distance, and the test image is matched to that set.

If the training data does not include multiple clusters, at least for this organ, or in general if there is not a plurality of sets of organ intensity characteristics but only a single set, then there is no need to match the test image to a set of organ intensity characteristics, for purposes of segmenting this organ, but the single set of organ intensity characteristics is used.

At 812, the training histogram for this cluster and target organ is read into the computer performing the segmentation. At 814, the training histogram is multiplied by the test histogram found in 808, for the different values of voxel intensity, and optionally normalized to the height of its highest peak, to find a posterior probability histogram. The posterior probability histogram is a histogram of the intensities in the bounding region found for the target organ in the test image, but with an enhancement of peaks at values of intensity that are usually associated with voxels in the target organ, and with a suppression of peaks at values of intensity that are usually associated with voxels that are in the bounding region of the target organ but outside the target organ itself.

Figure 9A:
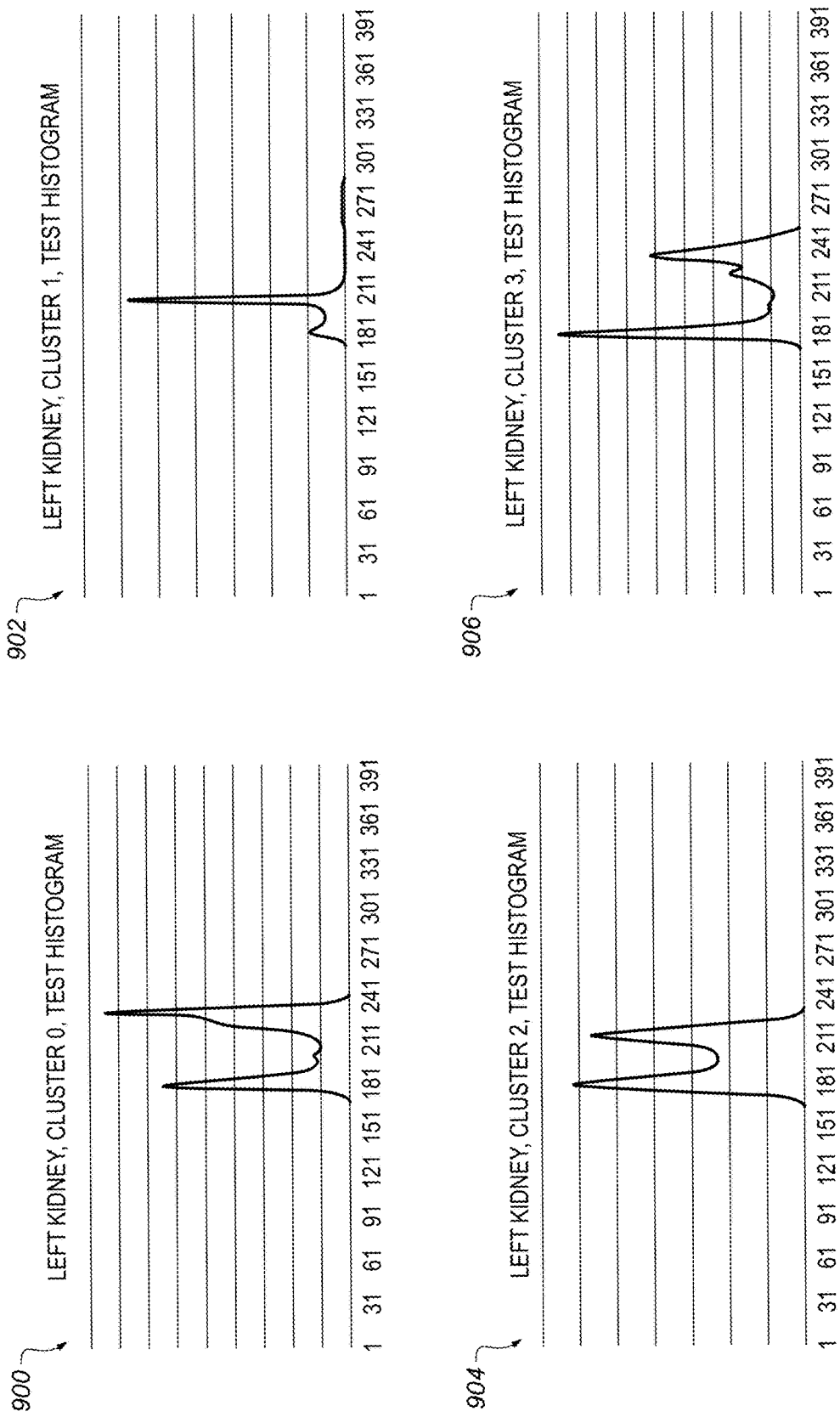
FIG. 9A shows examples of weighted test histograms obtained from medical images assigned to each of four clusters, segmented according to the method of FIG. 8.

FIG. 9A shows plots 900, 902, 904 and 906 of a test histogram for the left kidney, found for four different test images, respectively assigned to cluster 0, cluster 1, cluster 2, and cluster 3, using the method described above for 808 in FIG. 8. As in the training histograms shown in FIG. 5A, in plots 900, 902, 904 and 906 the horizontal axis shows the bin number for the intensity values, which range from −990 HU to +1000 HU, each bin being 5 HU wide. The scale of the vertical axis is arbitrary. There are two main peaks in each of the test histograms. Although the data that went into the histogram was weighted by the probability of the voxel being inside the left kidney, based on a probabilistic atlas, there is some variation in the location of the boundaries of the left kidney in different images, so the test histograms in FIG. 9A have some contributions from voxels in the vicinity of the spleen but outside the left kidney. The two main peaks in each of histograms 900, 902, 904 and 906 likely represent voxels inside the kidney (the peak on the right) and voxels just outside the kidney (the peak on the left). The smaller middle peak in plot 906 may represent an inner portion of the kidney that, with the large amount of contrast agent used in cluster 3 images, has a substantially different intensity than the outer portion of the kidney, as may be seen in image 206 in FIG. 2.

Figure 9B:
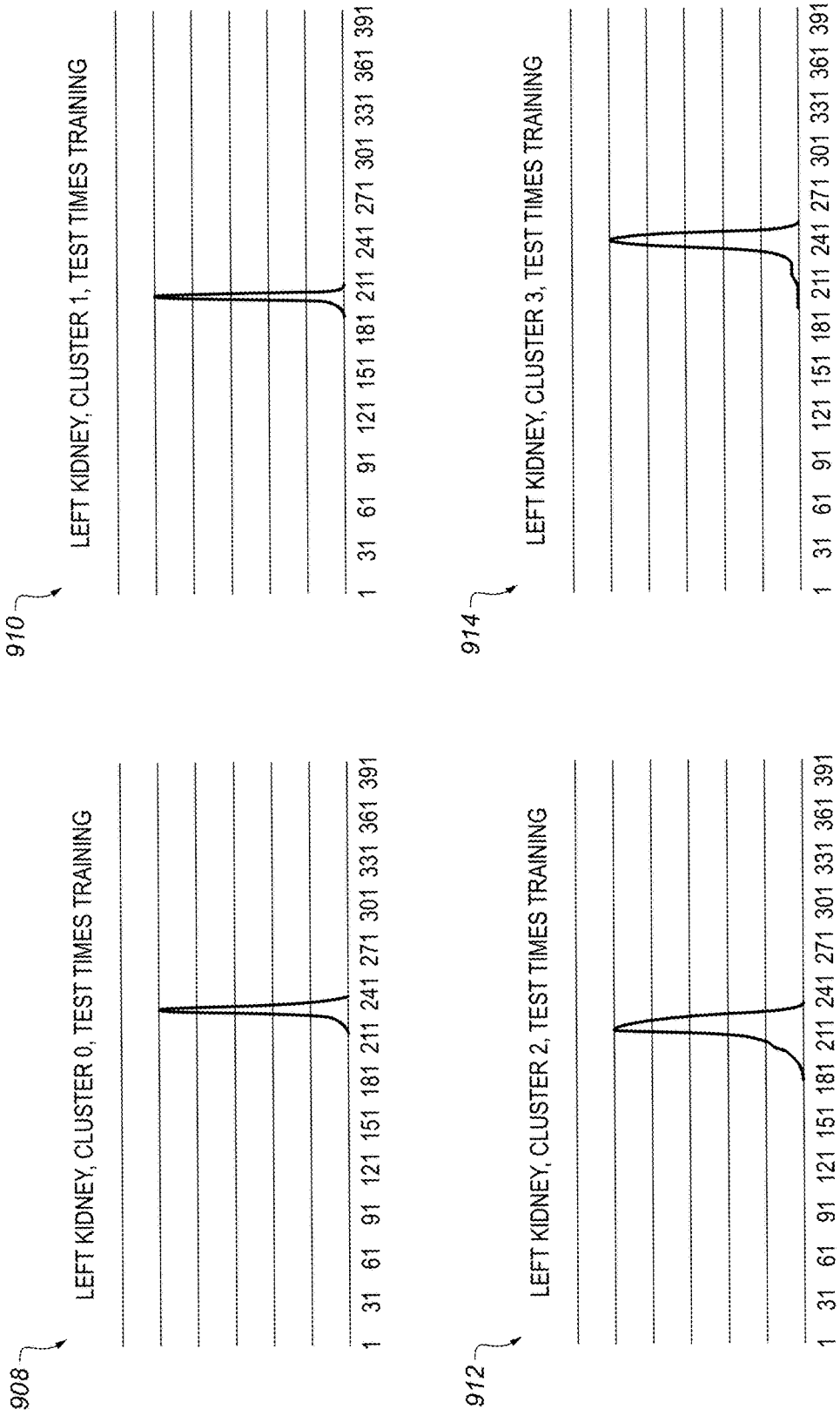
FIG. 9B shows each of the test histograms shown in FIG. 9A multiplied by the corresponding training histogram for that cluster shown in FIG. 5A, resulting in posterior probability histograms for each of the four clusters, according to the method of FIG. 8.

Multiplying the test histogram in each of plots 900, 902, 904 and 906 by the training histogram of the corresponding cluster shown in FIG. 5A, provides a posterior probability histogram, shown in FIG. 9B, in plots 908, 910, 912, and 914. Each of the posterior probability histograms has only a single main peak, corresponding to the peak in the test histogram for that cluster that is due to voxels inside the kidney. The other peak in each of the test histograms shown in FIG. 9A does not appear in the posterior probability histograms shown in FIG. 9B, because the training histograms have very low amplitude for intensity values that are largely found outside the left kidney within the left kidney bounding region. But plot 914, for cluster 3, still shows the smaller peak, seen in plot 906 of FIG. 9A, corresponding to voxels in the inner region of the kidney. Optionally, each of the posterior probability histograms is normalized by dividing them by its peak value, so that it ranges from 0 to 1, which will be useful later.

At 816, the intensity value at the highest point of the posterior probability histogram, the top of the peaks in each of the plots in FIG. 9B, is found, as well as a measure of the width of the peak around the highest point, for example the standard deviation of the peak, or its full width at half maximum. At 818, a mask is created, within the bounding region of the target organ in this image, of voxels with intensities within a range predicted as likely for the target organ, for example within half a standard deviation of the peak of the posterior probability histogram, or within the width of the peak at half maximum. Optionally, the mask is based on a slightly smoothed version of the image, even if the training and test histograms are based on unsmoothed images. Using a slightly smoothed image for creating the mask at 818 has the potential advantage that the mask will be less likely to include isolated voxels from nearby organs, which, due to noise, have an intensity value that is typical of the target organ, instead of an intensity value typical of the organ that they belong to. It should be understood that the method used for creating the mask at 818 is not necessarily intended to produce a mask that covers the entire target organ, even approximately, but rather is intended to produce a mask that covers at least a core region of the organ, and excludes voxels that do not belong to the organ. In a case where the organ includes two regions with very different intensities, such as the inner and outer parts of the kidney which may have very different intensities when contrast agent is used, it is especially likely that the mask created at 818 will not cover the entire organ, but only a part of the organ.

At 820, the mask generated in 818 is optionally morphologically improved, for example filling in holes in its interior that are completely surrounded by mask voxels, or filling in holes that are completely surrounded by mask voxels within a slice at a particular orientation, for example within an axial slice, or that are completely surrounded by mask voxels within a slice in any principal orientation (axial, coronal, or sagittal), or that are completely surrounded by mask voxels within a slice in either of two principal orientations, or in any two principal orientations, or in all three principal orientations. Such holes may result from noise in the image, as well as from small blood vessels, liver bile ducts, or other small features inside the target organ, that have a different intensity than most of the voxels of the target organ but are still considered part of the target organ. An example of a specific procedure for morphologically improving the mask, which the inventors have found gives good results at least for abdominal organs is as follows: 1) The mask is morphologically closed by 2 mm, to include small interior islands of different intensity value, perhaps due to noise. "Morphologically closing by 2 mm" means dilating by 2 mm, and then eroding by 2 mm. 2) Morphologically opening the mask by 5 mm, to disconnect nearby organs. "Morphologically opening by 5 mm" means eroding by 5 mm, and then dilating by 5 mm. However, if the morphological opening deletes the entire mask, then it is undone. 3) Deleting any components that are smaller than 4000 cubic millimeters in volume, but only if there is a remaining component that is more than 4000 cubic millimeters in volume. 4) Filling in any cavities that are completely surrounded by mask voxels in their axial slice. This adds to the mask some blood vessels, liver bile ducts, lesions, cysts, and low intensity regions in the middle of kidneys whose outer regions have much higher intensity when contrast agent is used. The resulting mask, after the morphological improvements, may be considered a rough segmentation of the target organ, in this image.

At 822, a seed voxel is found for segmenting the organ, inside the rough segmentation found at 820. Optionally, if a probabilistic atlas is used, the seed is found in a part of the rough segmentation that has the maximum probability value in the probabilistic atlas, or by looking at a part of the rough segmentation that has relatively high probability values in the probabilistic atlas. As used herein, "core region" sometimes refers to the maximum probability region or high probability region of the rough segmentation mask found at 818, rather than to the entire rough segmentation mask. In all the cases tested by the inventors, the maximum probability region of the rough segmentation has always had a probability of 100%, but this is not a necessary condition for the method to work. The maximum probability region, or high probability region, of the rough segmentation gives a set of voxels that are extremely likely to be within the target organ, based both on the intensity and the location of the voxels, and are thus useful to use as seeds for segmenting the organ using a region-growing algorithm. Although the rough segmentation alone is optionally used to find the seed voxel, using the maximum probability region of the rough segmentation has been found by the inventors to give better results, because it usually prevents a situation where the seed voxel is in a nearby organ, that extends into the bounding region of the target organ, and has similar intensity values to the target organ. Such a nearby organ is likely to be in a part of the bounding region for the target organ that has low probability in the probabilistic atlas, so can often be excluded by taking into account the information in the probabilistic atlas.

Optionally, the seed is a voxel that corresponds to the location most likely to fall within the target organ found at 430 of FIG. 4, and mapped from the probabilistic atlas to the bounding region of the target organ in this image. If the voxel is outside the rough segmentation, then optionally a voxel nearest to that voxel, within the rough segmentation, is chosen as the seed. Alternatively, the seed is a voxel furthest from the boundary of the maximum probability region of the rough segmentation, or furthest from the boundary of the rough segmentation. Alternatively, the seed is a voxel furthest from the boundary of the rough segmentation, that falls within the maximum probability region of the rough segmentation. The inventors have found that using a voxel furthest from the boundary of the maximum probability region of the rough segmentation often gives the best results of all these alternatives, since such a voxel is deep within both the rough segmentation, and the maximum probability region.

Optionally, instead of mapping the probabilities from the probabilistic atlas to the bounding region in the test image, and finding the seed voxel in the coordinates of the test image, the rough segmentation is mapped from the bounding region in the test image to the coordinates of the probabilistic atlas, the seed voxel is found in those coordinates, and is then mapped back to the coordinates of the test image. Although the two procedures are mathematically equivalent, working in the coordinates of the probabilistic atlas may be more computationally efficient. The following algorithm is an example of such a computationally efficient procedure for finding the seed: 1) an empty mask, called the "intersection mask" is created, with dimensions, in voxels, corresponding to the dimensions of the probabilistic atlas. 2). Look at each voxel in the probabilistic atlas, and find the closest voxel to its mapped location in the bounding region of the test image. If the closest voxel in the bounding region of the test image falls within the rough segmentation, and if the probability value of that voxel in the probabilistic atlas is at least as great as that of any voxel that has been included in the intersection mask so far, then add that voxel to the intersection mask, and update the highest probability value for any voxel included in the intersection mask so far, to the probability value for that voxel. 3). After doing this for each voxel in the probabilistic atlas, look again at each voxel in the intersection mask, and exclude from the intersection mask any voxel that has a probability value less than the maximum probability value of all voxels included in the intersection mask. 4). The voxel furthest from the boundary of the intersection mask is selected, the distance optionally defined not as the Euclidean distance in the space of the probability atlas, but as the Euclidean distance in the test image, taking into account the linear mapping of the probability atlas to the bounding region in the test image. 5). The closest voxel in the test image, to the location of the selected voxel in the intersection mask mapped into the test image, is designated as the seed voxel. It should be noted that this procedure will work even in the extreme case there the maximum probability value for any voxel in the rough segmentation is zero, in which case the seed voxel will be the voxel furthest from the boundary of the rough segmentation, but in practice, the maximum probability value of all voxels in the intersection mask is expected to be close to 100%. Optionally, if the maximum probability value is below some threshold, such as 90% or 80% or 50%, then the algorithm ends and generates a failure message, since in this case it is likely that either the bounding region or the training histogram for the target organ is completely wrong.

At 824, the seed voxel found in 822 is used to grow a more accurate segmentation of the target organ, using a region-growing algorithm, for example a fast-marching algorithm. Further details of the region-growing algorithm are given below in the description of FIG. 10.

At 826, one or more morphological filling operations are optionally performed on the more accurate segmentation found at 824. Optionally, the morphological filling operations include any of the filling operations described as optionally being performed at 820, for example adding to the segmentation all voxels that are entirely surrounded, in a slice in a particular orientation, for example an axial slice, by voxels that are already included in the segmentation. Such fill operations can add to the segmentation some blood vessels, bile ducts when the target organ is the liver, and low intensity regions in the interior of the organ when the target organ is a kidney, especially when contrast agent increases the intensity in an outer region of the kidney, but has less effect deeper in the interior of the kidney. Optionally, when the target organ is a kidney, voxels are added to the segmentation when they are entirely surrounded by voxels already in the kidney, in their coronal or sagittal slice, provided the intensity of the voxel has a posterior probability histogram value greater than a critical value, for example greater than 0.01, where, as described above, the posterior probability histogram has been normalized to its peak value. This procedure has been found to be effective at adding to the segmentation voxels deep in the interior of the kidney where contrast agent has not enhanced the intensity as much as in an outer portion of the kidney, while not adding to the segmentation voxels that are located outside the kidney, in the hollow of the kidney.

At 828, any leaks of the segmentation into nearby organs or other structures are optionally morphologically fixed, for example using a procedure such as described in provisional U.S. Ser. No. 62/144,552, titled "Organ Detection and Segmentation," filed on Apr. 8, 2015, incorporated herein in its entirety.

At 830, if there are more target organs to be segmented, then the next target organ is looked at, at 804. If all of the target organs have been segmented, then, at 832, any overlap regions between two segmented target organs are optionally found. Optionally, only pairs of target organs that are known to be commonly adjacent to each other, and/or have similar enough intensity distributions, are examined to see if their segmentations overlap, for example the spleen and the left kidney, the liver and the right kidney, or the liver and the spleen. Alternatively every pair of target organs is checked for overlap regions. The voxels in each of the overlap regions are then optionally assigned to one of the overlapping target organs, at 834, for example using a method described in provisional U.S. Ser. No. 62/144,552, titled "Organ Detection and Segmentation," filed on Apr. 8, 2015, incorporated herein in its entirety. In some cases even voxels that are not in overlap regions are reassigned to different organs, or are removed from the organ they are assigned to without assigning them to a different organ, as described in FIG. 10 of provisional application 62/144,552. Optionally, overlap regions are assigned to only one of the target organs, only if the overlap region is at least a minimum size, for example at least 100 cubic millimeters.

At 836, any region of a segmented organ, generally a small region, that has become disconnected from its seed, as a result of the reassignment of voxels in 834, is optionally removed from the segmentation of the organ. But optionally, this is not done if it would result in removing too large a fraction of the voxels in the segmentation of the organ, in particular if the seed no longer lies within the segmentation so that all voxels in the segmentation are disconnected from the seed. Optionally, removing disconnected regions for all target organs is done only after overlap voxels between all pairs of target organs have been found and assigned at 832 and 834. Alternatively, after overlap voxels for a given pair of target organs have been assigned, any resulting disconnected regions for those two target organs are removed, before finding and assigning overlap voxels for the next pair of target organs. At 838, any leaks of the segmentation of any organ into nearby organs or other structures, that may have appeared as a result of reassigning voxels in 834, are optionally morphologically fixed, for example using the same procedure as in 828.

At 840, a decision is optionally made whether to segment the target organs over again, in a new iteration, starting again at 804, using the present segmentation of target organs to find an improved bounding region for each target organ at 806. Optionally, a new iteration is always made after the first iteration, and iterations are repeated until a stopping criterion is reached, based for example on stopping the iterations when the difference in the segmentations between the last two iterations falls below a threshold, and/or stopping the iterations when the number of iterations has exceeded a maximum number. Performing more iterations can potentially produce a more accurate segmentation, since a more accurate bounding region may result in a more accurate intensity histograms and more accurate probabilities derived from the probabilistic atlas, which can lead to more accurate segmentations. Optionally, the bounding region of a target organ for the new iteration is defined as the smallest rectangular box, aligned with the principal axes, that includes all of the voxels of the target organ found in the segmentation in the previous iteration. Alternatively, the bounding region of a target organ for the next iteration as the smallest rectangular box that in some sense includes almost all of the voxels of target organ found in the segmentation in the previous iteration. For example, the bounding region is defined as a rectangular box, which extends, in each principal direction, from the $5^{th}$ percentile to the $95^{th}$ percentile of values of the coordinate for that principal direction for any voxels in the segmentation found in the previous iteration. Defining the bounding region in such a way may avoid outliers in the spatial distribution of voxels in the segmentation, that may result from any minor leaks that occurred during the segmentation procedure and were not properly fixed.

Alternatively, only a single iteration of the segmentation procedure is performed. The inventors have found that, for some applications of the method, the improved accuracy of segmentation that may result from using more than one iteration does not justify the increased computer time needed.

When no further iterations are to be done, the segmentation procedure ends at 842.

Region-Growing Algorithm

Figure 10:
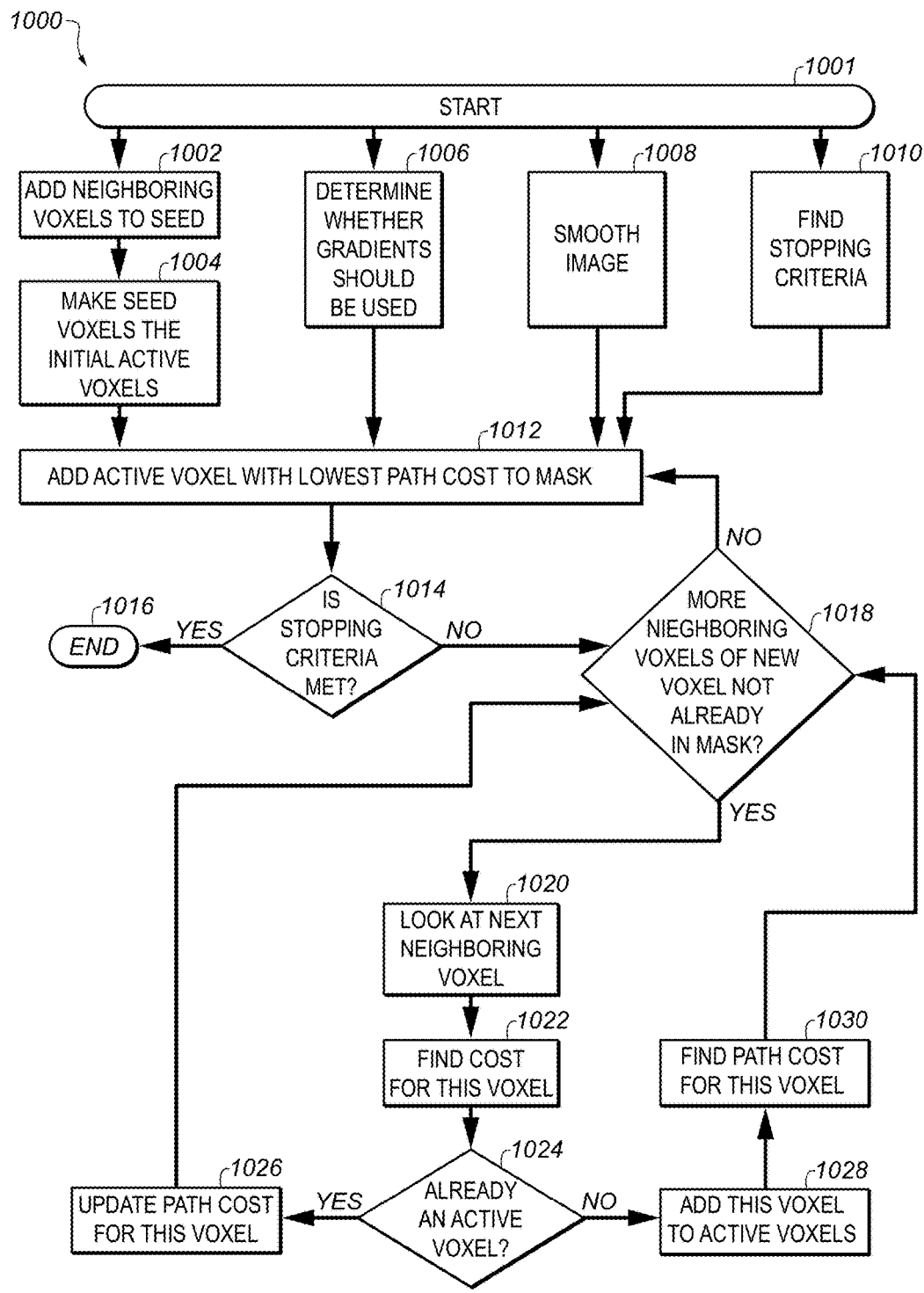
FIG. 10 is a flow chart, showing further details of growing a more accurate segmentation of the target organ according to the method of FIG. 8.

FIG. 10 shows a flow chart 1000, for a method of growing a more accurate segmentation of the target organ in a test image, using a region-growing algorithm, that is optionally used at 824 of FIG. 8. Region-growing algorithms are described by J. A. Sethian, *Level Set Methods and Fast Marching Methods: Evolving Interfaces in Computational Geometry, Fluid Mechanics, Computer Vision, and Materials Science* (Cambridge University Press, 1996). In a region-growing algorithm, such as a fast-marching algorithm or a Dijkstra algorithm, one or more seed voxels are initially assigned to a mask. The mask expands by adding to it active voxels, which are neighboring voxels to the voxels already in the mask, until a stopping criterion from a set of one or more predefined stopping criteria is reached. Each active voxel is assigned a cost function, which optionally is a local function of the voxel, depending for example on its intensity and position. From this cost function, a path cost is computed for the voxel, defined as the cost function integrated along the path of expansion from the one or more seed voxels to that voxel. The fast-marching and Dijkstra algorithms differ in how they define the path between voxels and hence the path cost, with the fast-marching algorithm allowing the path to be oriented obliquely with respect to the arrangement of voxels. The active voxels are ordered in order of ascending path cost, and at each iteration the active voxel with the lowest path cost is added to the mask. The stopping criterion is optionally based on the path cost. For example, the stopping criterion is optionally that the path cost for the voxel currently being added to the mask exceeds some maximum value, which means that all other active voxels have path cost at least that high.

In the method of flow chart 1000, a probabilistic atlas as described for example at 428 in FIG. 4, and included in the training data, is optionally used to evaluate the cost function at the voxels encountered by the growing segmentation mask. In addition, the cost function optionally depends on training data, such as the training histogram of intensities, and information on the distribution of intensity gradients, that is specific for the cluster that the test image has been assigned. Unlike standard fast-marching algorithms, for which the cost function is a local function of each voxel, in the method of flow chart 1000 the cost function optionally also depends on the volume to which the mask has grown so far.

The process for flow chart 1000 starts at 1001. Before beginning the fast-marching algorithm, four preliminary actions are optionally taken: 1002 followed by 1004, 1006, 1008, and 1010. These actions are optionally taken in parallel as shown in FIG. 10, or consecutively in any order, or some are performed in parallel and some consecutively. If performed consecutively, any of 1006, 1008 and 1010 are optionally performed between 1002 and 1004.

At 1002, one or more voxels are optionally added to the seed. For example, the four voxels that are adjacent to the seed voxel, in the axial slice of the seed voxel, are added to the seed voxel, and the region-growing algorithm begins from the additional voxels as well as from the original seed voxel. Enlarging the seed voxel in this way has the potential advantage of making the region-growing algorithm insensitive to the presence of noise which significantly changes the intensity of the seed voxel, so that it is outside the range of intensity expected for the test organ. If the seed is enlarged, so that it also includes a few other voxels at least one of which is not very affected by the noise, then the integrated cost function along a path from the seed to other voxels will not be substantially affected by the noise. This is potentially important when assigning voxels in an overlap region to one of the overlapping target organs, as described in provisional U.S. Ser. No. 62/144,552, titled "Organ Detection and Segmentation," filed on Apr. 8, 2015, incorporated herein by its entirety, since the path cost plays a role in deciding which target organ an overlap voxel should be assigned to.

At 1004, the seed voxels, including any neighboring voxels added to the seed at 1002, are made the initial active voxels for the fast marching algorithm, and nominally assigned a path cost of zero.

At 1006, a determination is optionally made whether or not the cost function, used in the region-growing algorithm, will depend on the local gradient of intensity. The gradient is optionally used if the gradients expected for the boundary voxels according to the training data, as shown for example in FIG. 5B, are sufficiently separated from the gradients expected for interior voxels according to the training data, for this organ. For example, optionally gradients are used if and only if the median gradient of boundary voxels is greater than the median gradient of interior voxels, plus 1.5 times the standard deviation gradient for interior voxels, for this target organ. The inventors have found that, in the tests done with segmenting abdominal organs, with various organ intensity characteristics, in the great majority of cases this condition was met, and gradients were included in the cost function.

Optionally, at 1008, the test image is slightly smoothed. For example, the intensity of each voxel is set equal to an average, possibly a weighted average, of the original intensity of the voxel and the intensity of its nearest neighbors, in three dimensions or only within a slice, for example within an axial slice. Such smoothing has the potential advantage that it may reduce noise which may cause voxels inside the target organ to have intensities that are not in the expected range for the target organ, but optionally the test image is not smoothed so much that the boundaries of the target organ are significantly blurred. Optionally, the smoothing uses anisotropic diffusion, which is greatest in directions perpendicular to the direction of the intensity gradient, to avoid blurring of the boundaries while still reducing noise. Optionally the image is not smoothed at all.

At 1010, a stopping criterion is found, for example a threshold value that the path cost of the voxel currently being added to the mask has to exceed, in order to stop expansion. Appropriate values of the path cost for the stopping criterion depend on how the cost of a voxel is defined, and exemplary choices for the stopping criterion will be discussed below, in the description of 1014, and examples are given of a cost function, in the description of FIG. 11. Optionally, the threshold value is chosen to be at least a few times higher than the path cost for most of the voxels, or almost all of the voxels, in the high probability region or maximum probability region of the rough segmentation optionally found at 822 of FIG. 8, for example at least 3 times higher, or at least 5 times higher, or at least 10 times higher. However, there may be a few voxels in this core region that have much higher path cost, because they are in small islands of atypical image intensity that were added to the rough segmentation by morphological improvements at 820 of FIG. 8, or because they are located in small islands of high probability and expected image intensity for the target organ, that are disconnected from the bulk of the core region. Those few atypical voxels may not have much lower path cost than the threshold value, and might even have higher path cost than the threshold value, even if a majority or great majority of voxels in the core region have much lower path cost than the threshold value.

Alternative or additional stopping criteria are also optionally used, for example the procedure optionally stops once a maximum total number of voxels has been added to the mask.

At 1012, the active voxel with the lowest path cost is added to the mask. If two or more active voxels share the lowest path cost, as will be true initially if there is more than one seed voxel with a path cost of zero, then one of them is chosen to add to the mask at this time.

At 1014 a decision is made whether the stopping criterion is satisfied. The stopping criterion is optionally that the path cost for the voxel that was added to the mask at 1012 is greater than a threshold, which means that the path cost is greater than the threshold for all active voxels. The threshold of the path cost for stopping is optionally set to be proportional to the cube root of the mean volume V expected for the target organ, from the training data. If the target organ were spherical, with volume V, then its radius would be $(3V/4\pi)^{1/3}$. The inventors have found that a threshold that works well, for the path cost, is $10(3V/4\pi)^{1/3}$, in the case where the gradient cost is used as part of the cost function, and with the cost function calculated as described below at the end of the description of FIG. 11. In the case where the gradient cost is not used as part of the cost function, because the boundary voxels are not clearly distinguished from the interior voxels by their higher intensity gradient, a lower threshold is optionally used for the path cost, for example $1.5(3V/4\pi)^{1/3}$, still with the same definition of cost function. It is potentially advantageous to use a lower threshold in this case, because an increase in intensity gradient will not stop the expansion at the boundary of the target organ, so it may be important to use a lower threshold for path cost, in order to stop the expansion before it leaks into a neighboring organ.

Optionally, an additional stopping condition is that there are no more active voxels. This would occur, for example, if the threshold were set so high that all of the voxels in the image are added to the mask, before any voxel has a path cost greater than the threshold. In practice, assuming that the test image does not consist entirely of voxels in the target organ, a lower threshold should be chosen, in order to obtain an accurate segmentation of the target organ, and the stopping condition would be met when there are still active voxels.

If the stopping criterion is satisfied, then no more voxels are added to the mask, and the fast marching algorithm ends at 1016.

If the stopping criterion is not satisfied, then at 1018, it is determined whether there are neighboring voxels to the new voxel added to the mask, that are not already in the mask and have not yet been considered. If there are no such neighboring voxels, then the next active voxel with the lowest path cost is added to the mask at 1012. If there are such neighboring voxels, then one of those neighboring voxels is considered at 1020. First, at 1022, the cost function is evaluated for that voxel. Details of how the cost function is evaluated, and how it optionally makes use of the probabilistic atlas, and of training data on intensity and intensity gradient for the cluster that the test image is assigned to, are given below in FIG. 11. In standard fast marching, it is not necessary to evaluate the cost function if the voxel is already an active voxel, which would have had its cost function evaluated before, but only if it is to be newly added to the active voxels, because the cost function depends only on local properties of the voxel and does not change as the fast marching proceeds. However, in the fast marching algorithm described by flow chart 1000, the cost function depends on the volume that the mask has reached so far, so the cost function may have changed even if it was evaluated previously. At 1024, it is determined if that neighboring voxel is already an active voxel. If it is, then at 1026, its path cost is updated. This is done by finding a tentative new path cost for it. In the case where the region-growing algorithm is a fast-marching algorithm, the tentative new path cost is found by solving an Eikonal equation, using the cost function of the voxel together with the path costs of all of its neighboring voxels that are already in the mask. A somewhat different definition of path cost is used for other region-growing algorithms, such as the Dijkstra algorithm. Further details on how the new path cost is calculated in the fast-marching algorithm and in related algorithms are provided on pages 86-100 of the book by Sethian referenced above. If the new path cost is lower than the old path cost of the neighboring voxel, then its path cost is lowered to the new value. If the old path cost is lower, then that value is kept. In this way, each active voxel always has the lowest path cost for any path connecting it to the seed, that has been explored so far.

If the neighboring voxel being considered is not already an active voxel, then it is made an active voxel at 1028. The path cost is found at 1030, by solving an Eikonal equation, using the cost function of the voxel together with the path costs of all of its neighboring voxels that are already in the mask, in the case where the region-growing algorithm is a fast-marching algorithm. Optionally, the active voxels are stored in the computer memory in a heap that is sorted by path cost, so that the active voxel with lowest path cost can be easily found at 1012, each time a voxel is to be added to the mask. In this case, the location of an active voxel in the heap is adjusted or initially determined after the path cost is found at 1026 or 1030.

After the path cost has been found for this neighboring voxel at 1030, or updated at 1026, a decision is again made at 1018 whether there are any more neighboring voxels, to the new voxel added to the mask, that are not already in the mask and have not yet been considered.

Figure 11:
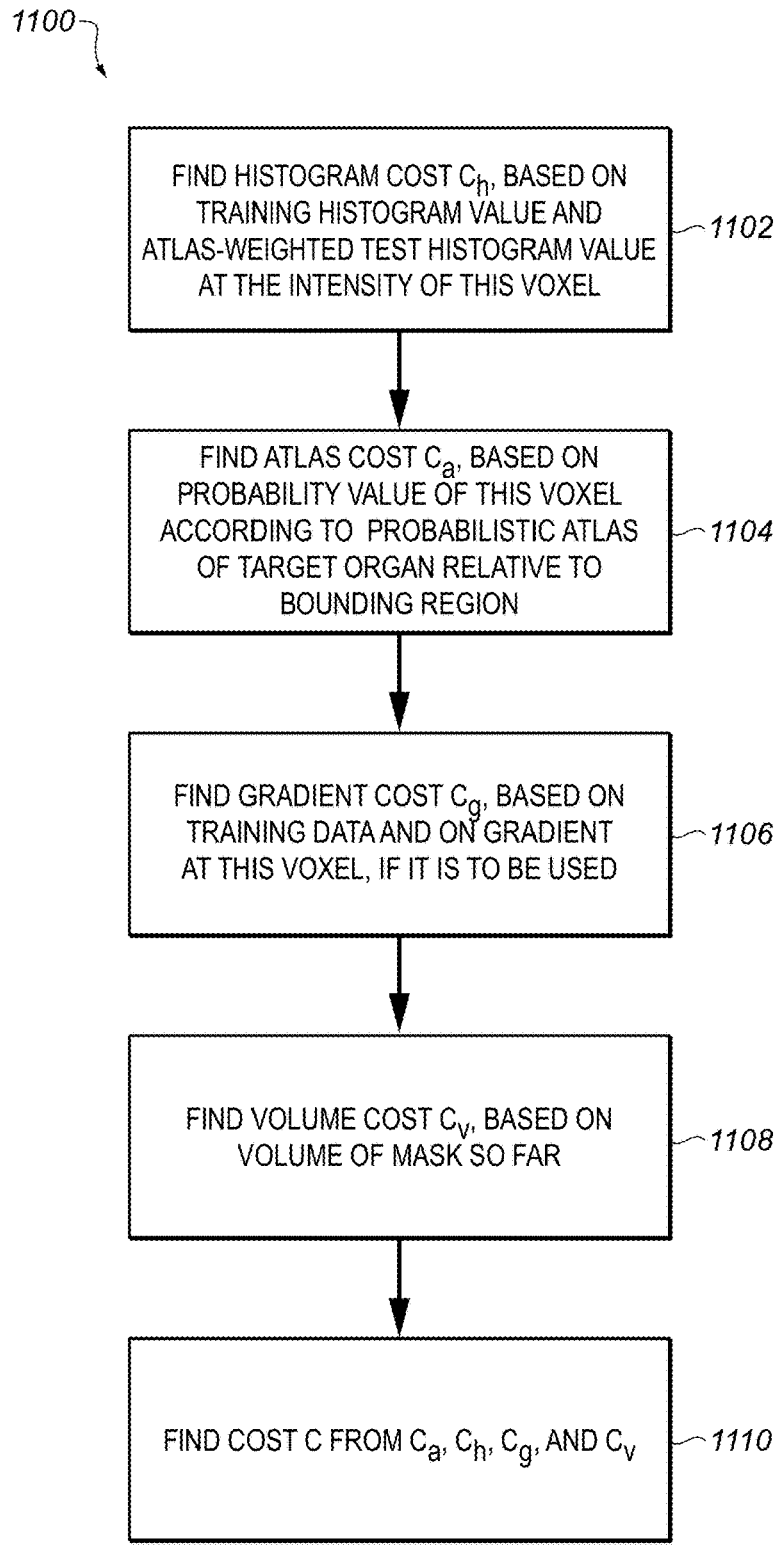
FIG. 11 is a flow chart, showing further details of finding the cost of a voxel according to the method of FIG. 10.

FIG. 11 shows a flow chart 1100 with further details of how the cost function of a voxel is evaluated at 1022 of FIG. 10. The cost function for each voxel optionally depends on one or more of the intensity of the voxel (histogram cost), the location of the voxel relative to the bounding region (atlas cost), the intensity gradient of the voxel (gradient cost), and total volume of the mask so far (volume cost). It should be understood that the intensity and intensity gradient refer to the smoothed image, if the image has been smoothed at 1008.

The histogram cost $C_h$ is evaluated at 1102, and is lower, for example, for voxels which have intensity values for which the posterior probability histogram is relatively high, than for voxels with intensity values for which the posterior probability histogram is relatively low. The probabilistic atlas optionally plays a role in evaluating the histogram cost, because the posterior probability histogram depends on the test histogram, which may be weighted according to the probabilistic atlas.

The atlas cost $C_a$ is evaluated at 1104, and is lower, for example, for voxels for which the probability for the corresponding voxel in the probabilistic atlas is relatively high, than for voxels for which the corresponding voxel in the probabilistic atlas is relatively low.

The gradient cost $C_g$ is evaluated at 1106, and is lower, for example, for voxels for which the intensity gradient is in a range expected for voxels in the interior of the organ, than for voxels for which the intensity gradient is much greater than expected for voxels in the interior. As noted above, the cost optionally does not depend on the intensity gradient at all if the ranges expected for voxels in the interior and at the boundary are too similar to each other, and in this case, the gradient cost is optionally not evaluated at all.

The volume cost $C_v$ is evaluated at 1108, and is lower, for example, for any voxel, if the volume of the mask so far is much less than the expected volume for the target organ, than if the volume of the mask so far is comparable to the expected volume, and the cost is optionally even higher if the volume of the mask so far is greater than the expected volume.

At 1110, the cost C of the voxel is found in terms of the histogram cost, the atlas cost, the gradient cost in some circumstances, and the volume cost.

Optionally, the voxels in a high probability core region of the target organ all have very low or zero cost. This has the potential advantage that all the voxels in the core region will be added to the mask with the path cost still well below the value required for the stopping criterion, and as a result, the set of voxels included in the final mask, when the expansion is finished everywhere, will be insensitive to the exact location of the seed. It also has the potential advantage that, when overlap voxels between two organs are assigned to one of the organs, as described in provisional application U.S. 62/144,552, titled "Organ Detection and Segmentation," filed on Apr. 8, 2015, incorporated herein in its entirety, based on their path cost for each of the organs, any voxel in the core region of the first organ and not in the core region of the second organ will have lower path cost for the first organ, even if the first organ is much larger in size than the second organ. For example, the cost function and stopping criterion are optionally defined so that a high probability core region covers at least 50% of the volume of the organ, or at least 75% of the volume, or at least 90% of the volume, with the core region defined as the voxels for which the path cost is no more than 5%, or no more than 10%, or no more than 20%, or no more than 30%, or no more than 50%, of the value of the path cost required for the stopping criterion.

The following procedure for finding the cost function of a voxel has been found by the inventors to work well, at least for some organs in the abdomen:

The histogram cost $C_h$ depends on the value of the posterior probability histogram at the intensity value of the voxel, in the original or smoothed image. If the value of the histogram, normalized to its peak value, is less than 0.0001, and at least 8 voxels have been added to the segmentation mask so far, then $C_h$ is set to be infinite, and hence the cost function is infinite, thus preventing the segmentation from entering such unlikely voxels. If fewer than 8 voxels have been added to the mask so far, however, an infinite cost function is not set for this voxel, to avoid having the segmentation end almost at the beginning, in case the seed happened to fall on a noisy patch of the image. Instead, the segmentation is given a chance to grow past this noisy patch into a less noisy region. For histogram value greater than 0.0001, or near the very beginning of the fast marching, $C_h$ is set equal to a positive power of the inverse of the posterior probability histogram value at the intensity value of the voxel, for example the square of the inverse of the posterior probability histogram value. This results in the cost rising rapidly as the intensity moves to values that are relatively more likely to be found outside the target organ, within the bounding region, and relatively less likely to be found in the target organ. In some embodiments of the invention, $C_h$ rises even more rapidly, for example like the fourth power of the inverse of the posterior probability histogram value, for subsequent iterations of the method shown in flow chart 800, with the bounding region revised according to the segmentation of the target organ found in the previous iteration. This is potentially advantageous, because the bounding region may be known more accurately in subsequent iterations, so the weighting according to the probabilistic atlas, which is used in finding the test histogram at 808 in FIG. 8, may be more accurate in subsequent iterations, and the resulting posterior probability histogram may be more reliable. Alternatively, $C_h$ is defined in the same way for subsequent iterations as for the first iteration, which has the potential advantage that inhomogeneities in intensity inside the target organ, for example due to blood vessels or lesions, will not be further penalized in subsequent iterations.

The atlas cost $C_a$ depends on whether the voxel is inside the bounding region, and if it is, it depends on the atlas probability of the voxel, which is defined as the probability of the nearest voxel in the probabilistic atlas to the location to which the voxel maps, using the linear mapping that maps the bounding region to the probabilistic atlas. In the first iteration of the procedure of flow chart 800, for voxels inside the bounding region, $C_a$ is set to −1 times the atlas probability. In the first iteration, for voxels outside the bounding region, $C_a$ is set to 0.2 times the Euclidean distance in millimeters between the voxel and the nearest voxel in the bounding region. This expression for $C_a$ outside the bounding region is motivated by the idea that since the bounding region found at 806 in FIG. 8 may be inaccurate and cut off small parts of the organ, the segmentation mask should be allowed to grow a small distance outside the bounding region, but it should be increasingly difficult for the segmentation mask to grow far outside the bounding region. For subsequent iterations, $C_a$ is set to 5 for voxels with atlas probability of 0, or for voxels outside the bounding region, and $C_a$ is set to 3 for voxels with atlas probability between 0 and 0.5. It is potentially advantageous to give a higher atlas cost to voxels that have relatively low probability, or are outside the bounding region, in subsequent iterations, because the bounding region is likely to be more accurate in subsequent iterations, and thus the atlas probability is expected to more accurately reflect where the target organ might be located.

If it was decided, at 1006, to use the intensity gradient in the cost, then the gradient cost $C_g$ depends on the intensity gradient magnitude of the voxel, defined in the same way as the intensity gradient magnitude was defined in 422 of FIG. 4, when finding the median and standard deviation of the intensity gradient magnitude in the training images, for internal and boundary voxels of the target organ. For example, the intensity gradient is optionally defined as the magnitude of the two-dimensional gradient in the axial slice of the voxel. If the magnitude of the gradient is less than the maximum normal inside gradient in the training data, defined as the median gradient for voxels inside the target organ, plus 1.5 times the standard deviation of the gradient for voxels inside the target organ, then $C_g$ is set to zero. If the magnitude of the gradient is greater than the maximum normal inside gradient, then $C_g$ is optionally given a positive value that depends linearly on the gradient for that voxel, for example going from 0 when the gradient is equal to the maximum normal inside gradient, to 20, or some other very high value, when the gradient is equal to the median gradient for boundary voxels in the training data. Making $C_g$ very high when the gradient is comparable to the median gradient for boundary voxels, has the potential advantage that it may tend to make the expansion reach the stopping condition when it reaches the boundary of the target organ, resulting in an accurate segmentation.

The volume cost $C_v$ differs from cost functions used in classical fast marching algorithms, because it is not a function only of the properties of the voxel, as the histogram, atlas, and gradient costs are, but it depends on the history of the expansion of the mask, because it depends on the volume of the mask so far, and because it depends on properties of distant voxels. Nevertheless, the inventors have found that using the volume cost often produces improved segmentation results, compared to not including the volume cost, and in particular it can help to prevent large leaks into neighboring organs that have similar intensity to the target organ. The volume cost $C_v$ optionally multiplies the other cost terms $C_h$, $C_a$, and $C_g$, in the formula used for the cost function. When the total volume of the mask is sufficiently small, for example less than the mean volume of the target organ minus the standard deviation of the volume of the target organ, in the training data, $C_v$ is optionally set to 1, so that the volume of the mask does not affect the cost. $C_v$ optionally rises slowly as the volume of mask increases from the mean volume minus the standard deviation of the volume, to the mean volume plus the standard deviation of the volume, and $C_v$ optionally rises more quickly as the volume of the mask increases above the mean volume plus the standard deviation of the volume. For example, $C_v$ is equal to 1 plus a function proportional to the square of the difference between the mask volume, and the mean volume minus the standard deviation of the volume in the training data, and $C_v$ reaches 8 when the mask volume is equal to the mean volume plus the standard deviation of the volume in the training data.

The cost function C for the voxel is optionally set equal to $C_v$ times $(C_h + C_a + C_g)$.

If the expansion is still near its beginning, for example if fewer than 8 voxels have been added to the segmentation mask so far, then the cost function is optionally never allowed to be greater than a maximum value, for example 10. This rule has been found to be potentially advantageous, because it may prevent the expansion from ending immediately after it starts, due to a noisy region around the seed, and it may ensure that a core region of the organ is entirely included in the mask, with voxels that have low path cost.

Image Processing System

Figure 12:
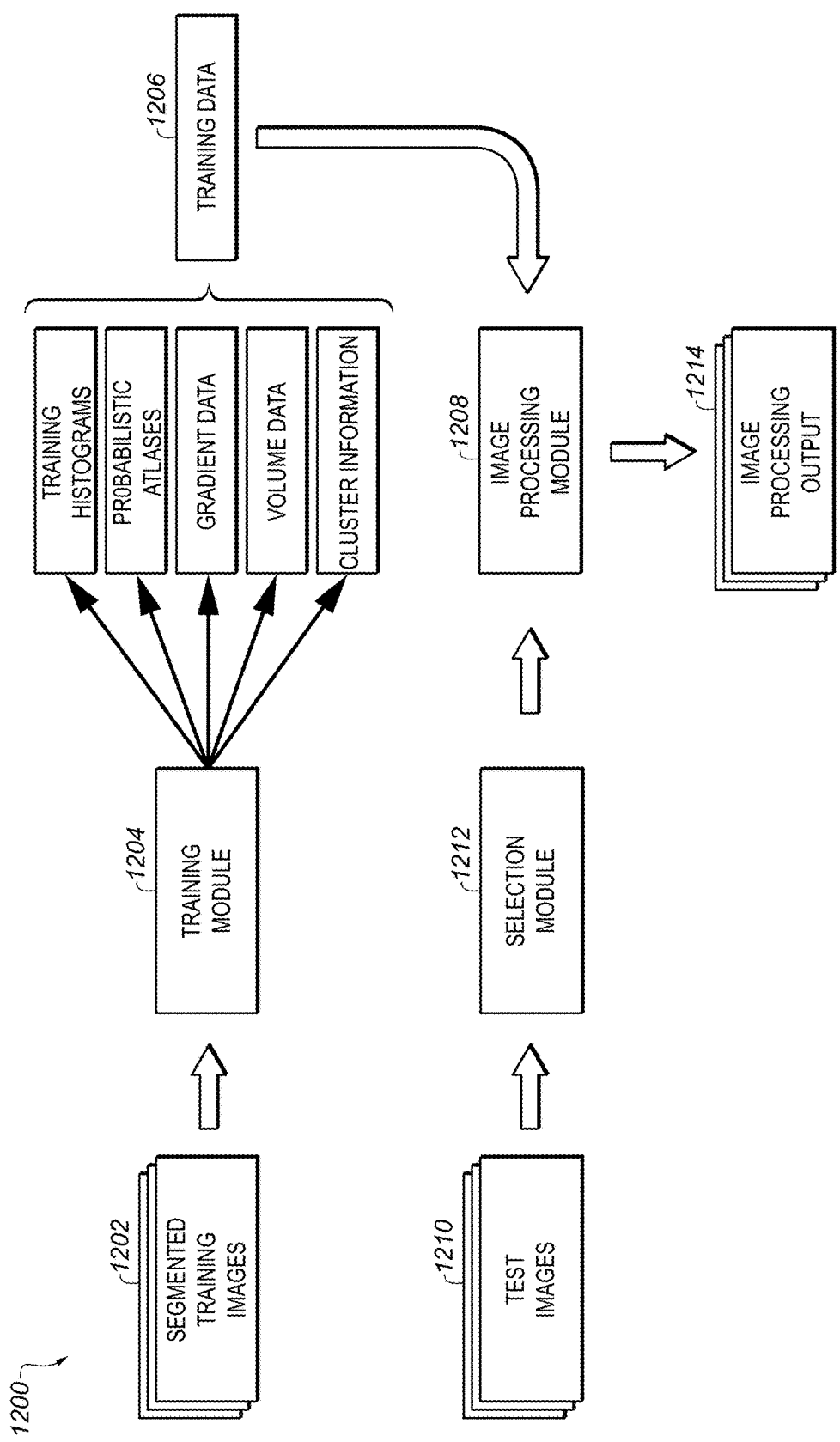
FIG. 12 is a block diagram showing a system for performing the method of FIG. 1, according to an exemplary embodiment of the invention.

FIG. 12 shows a block diagram for a system 1200, in the form of a data processor or computing device, using the approach outlined in FIG. 1, that can perform image processing, including segmentation, on a plurality of different target organs appearing in a database of medical images. A set 1202 of already segmented training images, showing the target organs, is used as input for a training module 1204. Images 1202 are in digital format, stored on a digital data storage device, such as a hard drive. The training module is, for example, a set of software instructions that a general purpose computer, or any other data processor or computing device, is programmed or otherwise configured to run, that produces training data 1206 as output using the training images, for example using the method shown in FIG. 4. The training data optionally includes one or more of training histograms, probabilistic atlases, gradient data, and volume data, for each target organ, stored on a digital data storage device, such as a hard drive, possibly incorporated into a software program supplied to an end user, for example on an optical disk, or on a server available for downloading. If clustering is used to group images with different organ intensity characteristics, then the training histograms and gradient data are optionally produced for each cluster for each target organ, and an average or representative intensity data, such as an average or representative intensity histogram, is optionally found and included in the training data for each cluster for each target organ, optionally for the entire bounding region of the target organ, so that test images can be assigned to a cluster.

In some embodiments of the invention, training module 1204, instead of generating training data 1206 from training images 1202, uses a different method of generating training data, for example from a model of what the organ intensity characteristics should look like. Regardless of how the training data is generated, it contains similar information about an expected appearance of the target organ in images, such as training histograms, probabilistic atlases, gradient data, and volume data for each target organ. Optionally, the training data 1206 generated by training module 1204 comprises a plurality of different sets of information about the appearance of the target organ, corresponding to different sets of organ intensity characteristics for the target organ in an image, that would be expected for different conditions of acquiring the image, for example associated with different results of contrast agent use or lack of use.

The training data is incorporated into an image processing module 1208, which can be run on a general purpose computer or any other computing device, programmed or otherwise configured to perform image processing of the target organs in test images, using the training data. For example, image processing module 1208 segments test images using the method shown in FIG. 8, including matching a test image to one of the sets of organ intensity characteristics, if training module 1204 generated a plurality of such sets in training data 1206. Test images 1210 are used as input for image processing module 1208. Test images 1210 are in a digital format, stored on a digital data storage device such as a hard drive. Optionally, a selection module 1212 automatically selects test images which include the target organs, or are expected to include the target organs. For example, if the target organs are in the abdomen, then the selection module selects test images with a field of view that includes the entire abdomen, or that includes all of the part of the abdomen where the target organs are located, or that is expected to include at least parts of the target organs. An example of a method that can be used to select such images is described above in FIG. 6, another method is described in U.S. Pat. No. 8,170,306 (Yu et al.), or any other method known in the art is optionally used. Image processing module 1208 uses training data 1206 to process test images 1210, at least the ones selected by selection module 1212, and outputs the result as image processing output 1214, for example segmentation masks of the target organ if the image processing comprises segmentation of the target organ. Image processing output 1214 is optionally displayed to a user on a graphic display device, for example segmentation masks may be overlayed on the test images, and/or the image processing output is stored on a digital storage device for later use, for example anisotropically smoothed images of the target organ in the test images are optionally used later as input images for segmentation. Alternatively, the image processing output is used immediately by an application, such as a segmentation module in the case of anisotropically smoothed output images. When the image processing comprises segmentation, the output segmentation masks may be used immediately, or later, to perform an automated statistical analysis of images acquired at a particular facility, that does not require ever displaying segmented images to a user, or even necessarily storing or transmitting the segmentation masks. Some applications for such automatically segmented images are described below.

Although the same computer is optionally used both for training module 1204 and image processing module 1208, often different computers are used, because the training data is optionally produced once, in order to incorporate it into an image processing program that can be used by the image processing module, and the image processing program may then be sold as a stand alone software product, which can be used by an end user to process test images on any computer.

The approach to image processing of organs, embodied in FIG. 1 and in FIG. 12, has several advantages:

The method is generic for many types of organs, and a new, unseen organ class may be added without making any changes to the code, simply by adding training examples of this organ. The inventors tested the generic nature of the algorithm, in the case where the image processing consists of segmentation, by initially working only on the spleen, left kidney, and right kidney, and then adding in the liver without changing the code. Equally good results were obtained on the liver, with no need to modify the algorithm, as on the organs used during algorithm development. Some data on these results is provided below, in the "Examples" section.

The method works well for images with widely variant fields of view, resolutions, contrast agent usage, noise levels, anomalies and pathologies, and other characteristics, as long as the training set is broad enough to encompass the desired range. Furthermore, the training set can always be broadened to better represent any class of test images that is found not to be segmented well.

The method for segmenting test images is very fast, on the order of a few seconds on a quad-core Intel Xeon 3.4 GHz computer, to segment four large abdominal organs, the liver, spleen, left kidney, and right kidney, including the preprocessing to predict organ bounding regions. It could be sped up even further with more careful optimization.

The method for image processing test images is fully automatic, requiring no user input, guidance, or interaction whatsoever, including automatically deciding the field of view of an unseen test image and assessing its relevance, so that the algorithm is run only on test images that include the target anatomy. It is therefore possible to run the algorithm as soon as the test image is saved after the patient is scanned, even before a radiologist loads the image to do the reading and reporting, so that the algorithm will run off-line and take up zero time from the user's point of view.

Applications of the Automatic Segmentation Method

The capability of the method of FIG. 1 to reliably and quickly segment organs in medical images with no human intervention makes it useful for a number of different applications:

Automatically detecting the organs included within an unseen scan, for use in automatically creating a searchable database of imaging studies containing various organs, or for use in gathering statistics of studies for a given hospital, or for use in gathering statistics on a given organ from a large body of organ segmentations.

Using the generated organ segmentation to allow automatic and optimal navigation such as panning, zooming, and/or windowing for each detected organ, based on its automatically-detected location, extent, and grayscale values.

Automatically finding all references in the radiology report to detected organs, optionally making use of natural language processing, and automatically turning the corresponding words in the report into hyperlinks, such that, when pressed, they navigate the user directly to the relevant organ, optionally also adjusting the zoom and/or windowing to optimize it for the current organ.

Creating a "per-organ windowing" display module so that, for example, when viewing any slice of a three-dimensional image, the user sees all voxels belonging to the liver with optimal or standard liver windowing parameters, all voxels belonging to the lungs with optimal or standard lung windowing parameters, etc. An example of such a "per-organ windowing" module is described, for example, in provisional application U.S. Ser. No. 61/974,077, titled "Organ-Specific Image Display", filed on Apr. 2, 2014, incorporated herein in its entirety. Optionally, the per-organ windowing parameters are selected differently for each cluster of images with similar organ intensity characteristics, if such clusters are used, to enable different windowing values depending on the presence of contrast agent. Optionally, if dual-energy CT scans are available, they are used to produce an optimal bone mask and to give those voxels bone windowing, by using the fact that a given bone voxel will differ in intensity, at the two x-ray energies, more than a non-bone voxel. Optionally, for example in scans without dual energy, a bone segmentation algorithm, such as any available in the literature, may be used to produce a bone mask for bone windowing.

Automatically computing the volume of each detected organ and optionally including the volumes in the report, and optionally triggering a warning when detecting an organ volume that is unusually large or small, to draw the radiologist's attention to a possible pathology.

Automatically dividing scans with a larger field of view into individual groups representing the chest, abdomen, and/or pelvis, a procedure which is currently carried out manually at many sites.

Upon loading an imaging study of a patient for whom there exist studies done at other times which the radiologist might wish to compare, using the body parts present in each group to automatically decide which groups to register with which, instead of waiting for user input as to which groups should be registered together.

Using each whole-organ segmentation as a starting point for more detailed segmentation of this organ, for example segmenting the lobes of the liver and lungs, segmenting the heart atriums and ventricles, segmenting the major blood vessels of each organ, and/or automatically finding lesions in each organ.

Automatically detecting the organ or other body part in which a user marking (for example, a user-generated graphic or a pathology segmentation) lies. This detection makes it possible to correctly label the user marking as belonging to the enclosing organ, for example in the radiology report. For example, if the radiologist draws a line within a liver lesion to measure its longest diameter, it is possible to automatically add to the report that this lesion is a liver lesion. After detecting the body part that each user marking falls in, a map or sketch of the human body is optionally drawn, highlighting the parts in which findings exist, optionally allowing navigation to the relevant findings by clicking on them in this map.

For this last application, lesions that lie on the boundary of an organ, but are excluded from its segmentation because they have very different intensity properties than the organ itself, can still be correctly detected as follows: After the end of the method of flow chart 800 in FIG. 8, when all of the target organs have been segmented, the segmentation mask of each organ is dilated by a short distance, for example 5 mm, but only into voxels that do not already belong to the mask of another organ. This dilation will add to the mask of each organ at least some of the voxels that belong to any lesions lying along the boundary of that organ thereby assuring that the mask overlaps the lesion. Optionally, the dilation only includes voxels with intensity values that are possible for such lesions, but excludes, for example, intensity values typical of the abdominal cavity, or intensity values typical of dense bones. However, including voxels that belong to the abdominal cavity will not matter very much, as long as voxels are not included in the dilation that belong to adjacent organs, on which a user marking might be placed. Then, if a user marking, and/or an automatic or semi-automatic lesion segmentation, sufficiently overlaps the dilated mask of an organ, because it is marking a lesion on the surface of the organ, it is optionally automatically labeled as belonging to that organ.

Although the description herein generally refers to detecting or segmenting or image processing of organs, it should be understood that the methods described herein can also be used for detecting or segmenting or image processing of any structures or objects in a medical image, such as lesions within an organ, or components of organs, or cavities or lumens inside hollow organs, or bones, or skeletal muscles. In some of these cases, the method may work better if it is modified. Some useful modifications, for the case of segmenting lesions on the surface of an organ, have already been described above.

For segmenting or other image processing of bones, and skeletal muscles, the bounding region is optionally not required to be aligned with the principle axes of the body, but is aligned with the expected axis of the bone, which for some bones may be very different from the principle axes of the body. Particularly for long bones of the limbs and their associated muscles, the orientation of the bone may vary greatly between images, and the orientation of the bone in the image is optionally determined or estimated from the test image, based for example on the high density portion of the bone, before the bounding region is found.

In the case of long thin lumens such as blood vessels, again the bounding region is optionally aligned with the expected axis of the blood vessel or lumen, rather than with the principle axes of the body, and in the case of blood vessels in the limbs, their orientation is optionally inferred from the orientation of corresponding bones in the limbs. Lumens which do not rigidly hold their shape, such as the lumens of the gastrointestinal tract, are optionally imaged when they are filled with a fluid, for example a fluid containing a contrast material such as barium in the case of CT images of the gastrointestinal tract, which will make their shape and internal intensity more predictable, and will make the lumen more visible.

For segmenting or other image processing of components of organs, such as lobes of the lungs or the liver, heart valves and heart chambers, and blood vessels that belong to organs, the organ is optionally segmented first, and a bounding box of the component of the organ is optionally found relative to the bounding box of the organ, or relative to a salient feature of the organ.

It is expected that during the life of a patent maturing from this application many relevant imaging modalities and region-growing algorithms will be developed and the scope of the terms "image" and "region-growing algorithm" are intended to include all such new technologies a priori.

As used herein, the term "providing" an item, for example a probabilistic atlas, includes obtaining that item in any way, including generating the item, or importing the item when it was previously generated by someone else.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Examples

Reference is now made to the following examples, which together with the above descriptions illustrate some embodiments of the invention in a non limiting fashion.

A fully automated segmentation system, as described above, was tested using 100 CT images of the abdomen that were acquired by various hospitals for a wide variety of purposes from a variety of patients, with a range of different imaging parameters such as field of view, resolution, x-ray energy, and contrast agent use. The spleen, left kidney, right kidney, and liver were used as target organs, and were manually segmented in all 100 images. Some of the images, for example 80 images, were then selected at random to be training images, and the other images were used as test images, to test the automated segmentation system against the manual segmentation, which was considered to be the true segmentation. For each of the test images, for each target organ, the coverage and the specificity were found. The coverage is defined here as the fraction of the volume of the true segmentation that was included in the segmentation mask found by the automated segmentation system.

The specificity is defined here as the fraction of the volume of the segmentation mask found by the automated segmentation system, that belongs to the true segmentation.

This test produced the following results, for median coverage and median specificity for each target organ, for the 20 test images:

| Target Organ | Median coverage | Median specificity |
| --- | --- | --- |
| Spleen | 95% | 100% |
| Left kidney | 94% | 100% |
| Right kidney | 95% | 99% |
| Liver | 95% | 99% |

The parameters used for the training and for segmentation were chosen to produce good results for the spleen, left kidney and right kidney, but without doing any tests to see how well the program performed for the liver. The completed program, with its parameters fixed, was then tested with the liver as a target organ, as well as with the spleen, left kidney, and right kidney. The fact that the median coverage and median specificity were about as high with the liver as they were with the other target organs suggests that the program will work well for other target organs as well, as long as training is done with those organs, without any need to further adjust the parameters of the program.

Applicants have described a method of finding medical images with a field of view expected to include a target organ in the abdomen, comprising: a) obtaining a plurality of medical images acquired from one or more subjects, at least some of the images having different fields of view, each of the images having known orientation with respect to the subject's body; b) automatically determining, in each of the images, whether or not the lungs are present, and automatically segmenting the lungs, at least roughly, if they are present; and c) automatically determining, from the contents of the images, including the presence or absence of the lungs and the location of the lungs if they are present, which images have a field of view that is expected to include the target organ, and which images do not.

In addition, at least some of the images obtained have one or more of different resolution, different image characteristics affected by contrast agent use of lack of use, and different noise level.

The method further comprises: a) automatically determining, from the contents of the images, which images have a field of view that includes both an abdomen region and a chest region, or which images have a field of view that includes both an abdomen region and a pelvis region, or which images have a field of view that includes both an abdomen region and one or both or a chest region and pelvis region, or which images have a field of view that includes a chest region, an abdomen region, and a pelvis region; and b) automatically dividing each of those images into a plurality of separate sub-images, each sub-image showing a different one of the regions, chest, abdomen or pelvis, determined to be in the field of view of the image.

In addition, wherein determining which images have a field of view that is expected to include the organ comprises: a) for those images that are determined to include at least part of the lungs, determining whether a bottom edge of the field of view of the image is at least a threshold distance below the lowest lung voxel; and b) if the bottom edge of the field of view is at least the threshold distance below the lowest lung voxel, determining that the field of view of the image is expected to include the target organ.

Still further, wherein determining which images have a field of view that is expected to include the organ comprises: a) for those images that are determined to include at least part of the lungs, determining whether a bottom edge of the field of view of the image is at least a threshold distance below the lowest lung voxel; and b) if the bottom edge of the field of view is less than the threshold distance below the lowest lung voxel, determining that the field of view is not expected to include the target organ.

In the method, the threshold distance can be between 30 and 40 cm, or alternately, between 28 and 38 cm.

In the method, the threshold area can be between 250 and 400 square centimeters.

In the method, wherein determining which images have a field of view that is expected to include the organ, the method further comprises: a) for those images that are determined not to include any of the lungs, determining whether a top edge of the field of view of the image is empty of any part of the subject's body; and b) if the top edge of the field of view is empty of any part of the subject's body, determining that the field of view is not expected to include the target organ.

In the method, wherein determining which images have a field of view that is expected to include the organ, the method further comprises: a) for those images that are determined not to include any of the lungs, attempting to obtain a segmentation of the large leg bones; b) for those images that are determined not to include any of the lungs, and that include the large leg bones according to the attempted segmentation of the large leg bones, determining whether a top edge of the image is at least a threshold distance above a highest voxel of the large leg bones; and c) for those images for which the top edge of the image is at least the threshold distance above the highest voxel of the large leg bones, determining that the field of view of the image is expected to include the target organ.

In the method, wherein determining which images have a field of view that is expected to include the organ, the method further comprises: a) for those images that are determined not to include any of the lungs, attempting to obtain a segmentation of the large leg bones; b) for those images that are determined not to include any of the lungs, and that do include the large leg bones according to the attempted segmentation of the large leg bones, determining whether a top edge of the image is at least a threshold distance above a highest voxel of the large leg bones; and c) for those images for which the top edge of the image is not at least the threshold distance above the highest voxel of the large leg bones, determining that the field of view of the image is not expected to include the target organ.

In the method, wherein determining which images have a field of view that is expected to include the organ, the method further comprises: a) for those images that are determined not to include any of the lungs, attempting to obtain a segmentation of the large leg bones; b) for those images that are determined not to include any of the lungs, and not to include any of the large leg bones, determining whether an axial slice of the image that contains a largest area of voxels that lie within the subject's body has an area of voxels within the subject's body greater than a threshold area; and c) for those images for which the largest area of voxels that lie within the subject's body is not greater than the threshold area, determining that the field of view of the image is not expected to include the target organ.

In the method, wherein determining which images have a field of view that is expected to include the organ, the methods further comprises: a) for those images that are determined not to include any of the lungs, attempting to obtain a segmentation of the large leg bones; b) for those images that are determined not to include any of the lungs, and not to include any of the large leg bones, determining whether an axial slice of the image that contains a largest area of voxels that lie within the subject's body has an area of voxels within the subject's body greater than a threshold area; and c) for those images for which the largest area of voxels that lie within the subject's body is greater than the threshold area, determining that the field of view of the image is expected to include the target organ.

Applicants have described a system for finding medical images with a field of view expected to include a target organ in the abdomen, the system comprising: a) an input device that receives digital medical images of one or more subjects, including information on an orientation of each image with respect to the subject's body; and b) a data processor with access to the medical images, programmed to: i) determine, in each of the images, whether or not the lungs are present, and to segment the lungs, at least roughly, if they are present; and ii) determine, from the contents of the images, including the presence or absence of the lungs and the location of the lungs if they are present, which images have a field of view that is expected to include the target organ, and which images do not.

Applicants have described a method of automatically selecting for registration medical images covering a selected region of a subject's body, the method comprising: a) providing a plurality of medical images of the subject, some of which cover the selected region of the subject's body, and at least one of which covers a different region of the subject's body and does not cover the selected region; b) automatically determining, from the contents of the images, which of the images cover the selected region; and c) selecting for registration the images covering the selected region.

The method can further comprise automatically registering the images selected for registration.

In the method, wherein the selected region is the abdomen, the provided medical images have known orientation with respect to the subject's body, and automatically determining which images cover the selected region, the method further comprises: a) automatically determining, in each of the images, whether or not the lungs are present, and automatically segmenting the lungs, at least roughly, if they are present; and b) automatically determining, from the contents of the images, including the presence or absence of the lungs and the location of the lungs if they are present, which images have a field of view that is expected to include the abdomen, and which images do not.

Applicants have described a system for automatically selecting for registration medical images covering a selected region of a subject's body, the system comprising: a) an input device that receives digital medical images; and b) a data processor with access to the medical images, programmed to: i) determine, from the contents of the images, which of the images cover the selected region; and ii) select for registration the images covering the selected region.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of processing a medical image comprising an organ, the method comprising:
   a) obtaining a medical image;
   b) automatically estimating one or more organ intensity characteristics in the image, from contents of a region of the image that appears to correspond, at least in part, to at least a portion of the organ;
   c) providing a plurality of sets of organ intensity characteristics, each set different example of possible intensity characteristics of the organ;
   d) choosing one of the plurality of sets, that has organ intensity characteristics that provide a better match than one or more other sets to the estimated organ intensity characteristics of the image;
   e) setting values of one or more image processing parameters based on the organ intensity characteristics of the chosen set; and
   f) automatically processing the image using said values of image processing parameters, the processing comprising segmenting the organ in the image by using information, obtained by evaluating a local characteristic of one or more voxels in the image, on whether the voxels are likely to belong to the organ, based on the organ intensity characteristics of the chosen set.

2. The method according to claim 1, wherein choosing one of the plurality of sets or organ intensity characteristics is done automatically, using as input data the estimated one or more organ intensity characteristics, and data defining the plurality of sets of organ intensity characteristics.

3. The method according to claim 1, wherein two or more of the sets are generated from a plurality of training images acquired from subjects under different conditions and grouped in clusters, each of the two or more sets generated from a different cluster of the training images.

4. The method according to claim 3, further comprising:
   a) obtaining information about organ intensity characteristics for each of the training images;
   b) grouping the training images into clusters according to the information about organ intensity characteristics; and
   c) for each of a plurality of the clusters, finding representative information about the organ intensity characteristics for the training images in that cluster;
   wherein providing the sets of organ intensity characteristics comprises providing the representative information for the training images in the cluster that each set is generated from, for the sets that are generated from the training images.

5. The method according to claim 1, wherein estimating the organ intensity characteristics comprises determining information on image texture from the contents of the image in the region.

6. The method according to claim 1, wherein estimating the organ intensity characteristics comprises determining information on an intensity distribution of voxels from the contents of the image in the region, the sets of organ intensity characteristics comprise information on intensity distributions of voxels, and choosing one of the sets comprises choosing a set for which the information on an intensity distribution provides a better match than the information on an intensity distribution of another set to the information intensity distribution of voxels in the region of the image.

7. The method according to claim 6, wherein choosing a set for which the information on an intensity distribution of voxels provides a better match to the information on an intensity distribution of voxels in the region comprises choosing a set for which the information on an intensity distribution of voxels provides a better match of a plurality of independent parameters.

8. The method according to claim 1, wherein at least two of the sets of organ intensity characteristics differ from each other in exemplifying different results of contrast agent use or lack of use in the organ, and choosing one of the sets comprises choosing a set which exemplifies results of contrast agent use or lack of use that provide a better match than one or, more other sets to the results of contrast agent use or lack of use in the image.

9. The method according to claim 8, wherein the image processing parameters comprise one or more of information on a distribution of voxel intensities, and information on a distribution of voxel intensity gradients, specific to the chosen set of organ intensity characteristics.

10. The method according to claim 9, wherein the image processing parameters comprise information on a distribution of magnitudes of intensity gradient expected in an interior of the organ, and information on a distribution of magnitudes of intensity gradient expected along a boundary of the organ, specific to the chosen set of organ intensity characteristics.

11. The method according to claim 1, wherein the different sets of organ intensity characteristics differ from each other in exemplifying different results of contrast agent use or lack of use in the organ, choosing one of the sets comprises choosing a set exemplifying results of contrast agent use or lack of use that provide a better match than one or more other sets to the results of contrast agent use or lack of use in the image, and evaluating the local characteristic comprises evaluating whether the one or more voxels are likely to belong to the organ based on whether their intensity, intensity gradient, or both, are within a range expected for voxels of the organ according to the training images of the chosen cluster, and segmenting the organ comprises finding a core region of voxels that are likely to belong to the organ according to said evaluation.

12. The method according to claim 1, wherein the different sets of organ intensity characteristics differ from each other in exemplifying different results of contrast agent use or lack of use in the organ, choosing one of the sets comprises choosing a set exemplifying results of contrast agent use or lack of use that provide a better match than one or more other sets to the results of contrast agent use or lack of use in the image, and evaluating the local characteristic of a voxel comprises evaluating a cost function that depends on a degree of similarity of one or more of the intensity and the intensity gradient of the voxel to values expected for voxels of the organ according to the training images of the chosen cluster, and segmenting the organ comprises using a region-growing algorithm with said cost function.

13. The method according to claim 1, wherein processing the image comprises changing the intensity values of one or more voxels of the image.

14. The method according to claim 13, wherein the image processing parameters comprise an expected minimum magnitude of intensity gradient at the edge of the organ, and processing the image comprises anisotropically smoothing the image with less smoothing along an intensity gradient that is greater than the expected minimum magnitude than perpendicular to the intensity gradient.

15. The method according to claim 13, wherein the image processing parameters comprise a range of intensity for which the organ has structure that would be more easily visible if the contrast were increased in that range, and processing the image comprises increasing the contrast in that range.

16. A system for processing a medical image comprising an organ, the system comprising:
 a) a data storage device that stores a digital test image;
 b) a data storage device, the same as or different from the device that stores the digital test image, that stores data defining a plurality of sets of organ intensity characteristics, each set a different example of possible intensity characteristics of the organ; and
 c) a data processor with access to the test image and the data defining the sets of organ intensity characteristics, programmed to:
  i) estimate one or more organ intensity characteristics in the image, from contents of a region of the image that appears to correspond, at least in part, to at least a portion of the organ;
  ii) obtain a choice of one of the plurality of sets, that has organ intensity characteristics that provide a better match than one or more other sets to the estimated organ intensity characteristics of the image;
  iii) set values of one or more image processing parameters based on the organ intensity characteristics of the chosen set; and
  iv) process the image using said values of image processing parameters, the processing comprising segmenting the organ in the image by using information, obtained by evaluating a local characteristic of one or more voxels in the image, on whether the voxels are likely to belong to the organ, based on the organ intensity characteristics of the chosen set.

17. The system according to claim 16, wherein the data, processor is programmed to obtain the choice of one of the plurality of sets by choosing one of the plurality of sets automatically, based on the estimated organ intensity characteristics of the image.

18. The system according to claim 16, also comprising a user interface, wherein the data processor is programmed to use input from a user through the user interface, to obtain the choice of one of the plurality of sets.

19. A method of processing a medical image comprising an organ, the method comprising:
 a) obtaining a medical image;
 b) automatically estimating one or more organ intensity characteristics in the image, from contents of a region of the image that appears to correspond, at, least in part, to at least a portion of the organ;
 c) providing a plurality of sets of organ intensity characteristics, each set a different example of possible intensity characteristics of the organ, exemplifying different results of contrast agent use or lack of use in the organ;
 d) choosing one of the plurality of sets, that has organ intensity characteristics that provide a better match than one or more other sets to the estimated organ intensity characteristics of the image;
 e) setting values of one or more image processing parameters based on the organ intensity characteristics of the chosen set; and
 f) automatically processing the image using said values of image processing parameters, the processing comprising changing the intensity values of one or more voxels of the image.

* * * * *